(12) United States Patent
Gasparyan et al.

(10) Patent No.: US 9,700,697 B2
(45) Date of Patent: Jul. 11, 2017

(54) INTRAVASCULAR CATHETER ASSEMBLY

(75) Inventors: Levon Gasparyan, Helsinki (FI); Hans Romberg, Stutensee (DE)

(73) Assignee: OPTOMEDITECH OY, Helsinki (FI)

( * ) Notice: Subject to any disclaimer, the term of this patent is extended or adjusted under 35 U.S.C. 154(b) by 6 days.

(21) Appl. No.: 14/410,881

(22) PCT Filed: Aug. 21, 2012

(86) PCT No.: PCT/EP2012/066246
§ 371 (c)(1),
(2), (4) Date: Dec. 23, 2014

(87) PCT Pub. No.: WO2014/029423
PCT Pub. Date: Feb. 27, 2014

(65) Prior Publication Data
US 2015/0314105 A1 Nov. 5, 2015

(51) Int. Cl.
*A61M 25/01* (2006.01)
*A61M 5/42* (2006.01)
(Continued)

(52) U.S. Cl.
CPC ....... *A61M 25/0105* (2013.01); *A61B 5/1535* (2013.01); *A61B 5/150748* (2013.01);
(Continued)

(58) Field of Classification Search
CPC ............ A61B 5/1422; A61B 5/150748; A61B 5/1535; A61B 5/155; A61B 5/15003;
(Continued)

(56) References Cited

U.S. PATENT DOCUMENTS 2,092,929 A 9/1937 Ovington
3,071,135 A 1/1963 Baldwin et al.
(Continued)

FOREIGN PATENT DOCUMENTS

EP 1884211 A2 2/2008
EP 2449994 A1 5/2012
(Continued)

OTHER PUBLICATIONS

International Search Report was mailed on Jul. 30, 2013 for International Application No. PCT/EP2012/066246 on Aug. 21, 2012 and published as WO/2014/029423 on Feb. 27, 2014 (Inventor—Gasparyan et al)(6 pages).
(Continued)

*Primary Examiner* — Imani Hayman
*Assistant Examiner* — Nilay Shah
(74) *Attorney, Agent, or Firm* — Ballard Spahr LLP

(57) ABSTRACT

A peripheral intravascular catheter assembly comprising a tubular introducer needle and an adapter connected to the proximal end of the light guide. An introducer needle comprises a connection hub and a needle member. The needle member has a lumen, a distal end and a proximal end. The assembly can include a cannula tubing surrounding at least a portion of the needle member, with at least one light source and with an electronic module, configured to power the light source. The light guide has a distal end and a proximal end and extends along the lumen of the needle member. The adapter may be connected to the electronic module to the connection hub of the introducer needle so that light emitted by the light source is capable of entering the light guide, but blood flowing through the lumen of the needle member is prevented from contacting the light source.

20 Claims, 25 Drawing Sheets

201

(51) Int. Cl.
  *A61M 5/46*   (2006.01)
  *A61B 5/153*  (2006.01)
  *A61M 25/06*  (2006.01)
  *A61B 5/15*   (2006.01)
  *A61B 5/155*  (2006.01)

(52) U.S. Cl.
  CPC .............. *A61M 5/427* (2013.01); *A61M 5/46* (2013.01); *A61M 25/0606* (2013.01); *A61M 25/0693* (2013.01); *A61B 5/1422* (2013.01); *A61B 5/15003* (2013.01); *A61B 5/155* (2013.01); *A61B 5/15016* (2013.01); *A61B 5/150389* (2013.01); *A61B 5/150503* (2013.01); *A61B 5/150992* (2013.01); *A61M 25/0618* (2013.01); *A61M 2025/0166* (2013.01)

(58) Field of Classification Search
  CPC . A61B 18/18; A61B 2018/1807; A61B 18/20; A61B 2018/2005; A61B 18/201; A61M 5/427; A61M 5/46
  See application file for complete search history.

(56) References Cited

U.S. PATENT DOCUMENTS

| | | | |
|---|---|---|---|
| 3,556,085 A | | 1/1971 | Takahashi |
| 4,269,192 A | | 5/1981 | Matsuo |
| 4,311,138 A | | 1/1982 | Sugarman |
| 4,566,438 A | | 1/1986 | Liese et al. |
| 4,945,895 A | * | 8/1990 | Takai ................. A61B 1/07 600/104 |
| 4,971,068 A | | 11/1990 | Sahi |
| 5,030,207 A | | 7/1991 | Mersch et al. |
| 5,060,207 A | | 10/1991 | Kaneda et al. |
| 5,137,518 A | | 8/1992 | Mersch |
| 5,314,410 A | | 5/1994 | Marks |
| 5,370,640 A | * | 12/1994 | Kolff ................... A61B 5/0084 604/21 |
| 5,385,572 A | | 1/1995 | Nobles et al. |
| 5,460,182 A | | 10/1995 | Goodman et al. |
| 5,954,701 A | | 9/1999 | Matalon |
| 7,918,805 B2 | | 4/2011 | Chelak |
| 2002/0115922 A1 | * | 8/2002 | Waner .................. A61B 5/0059 600/407 |
| 2003/0114842 A1 | | 6/2003 | DiStefano |
| 2003/0236517 A1 | * | 12/2003 | Appling ................. A61B 18/24 606/7 |
| 2007/0073160 A1 | * | 3/2007 | Imam .................... A61B 90/39 600/476 |
| 2007/0260298 A1 | * | 11/2007 | Naldoni ............... A61B 18/203 607/94 |
| 2008/0091104 A1 | | 4/2008 | Abraham |
| 2008/0097378 A1 | | 4/2008 | Zuckerman |
| 2008/0154217 A1 | | 6/2008 | Carrez et al. |
| 2008/0167577 A1 | | 7/2008 | Weilbacher et al. |
| 2009/0043225 A1 | | 2/2009 | Conway et al. |
| 2009/0088698 A1 | | 4/2009 | Steube |
| 2009/0149771 A1 | | 6/2009 | Myklebust et al. |
| 2009/0228002 A1 | * | 9/2009 | Rioux ................... A61B 18/18 606/33 |
| 2011/0009738 A1 | | 1/2011 | Zemel |
| 2011/0288405 A1 | | 11/2011 | Razavi et al. |
| 2014/0029421 A1 | | 1/2014 | Rajagopalan et al. |
| 2014/0155739 A1 | | 6/2014 | Manohar |

FOREIGN PATENT DOCUMENTS

| | | |
|---|---|---|
| FR | 2977497 A1 | 1/2013 |
| WO | WO-99/15074 A1 | 4/1999 |
| WO | WO-2006/091597 A1 | 8/2006 |
| WO | WO-2007/032992 A1 | 3/2007 |
| WO | WO-2004/000099 A2 | 2/2008 |
| WO | WO-2008/024478 A2 | 2/2008 |

OTHER PUBLICATIONS

Written Opinion was mailed on Jul. 30, 2013 for International Application No. PCT/EP2012/066246 on Aug. 21, 2012 and published as WO/2014/029423 on Feb. 27, 2014 (Inventor—Gasparyan et al) (13 pages).

International Preliminary Report on Patentability was mailed on Feb. 24, 2015 for International Application No. PCT/EP2012/066246 on Aug. 21, 2012 and published as WO/2014/029423 on Feb. 27, 2014 (Inventor—Gasparyan et al) (14 pages).

International Search Report was mailed on Mar. 18, 2013 for International Application No. PCT/EP2012/066243 on Aug. 21, 2012 and published as WO/2014/029421 on Feb. 27, 2014 (Inventor—Gasparyan et al) (5 pages).

Written Opinion was mailed on Mar. 18, 2013 for International Application No. PCT/EP2012/066243 on Aug. 21, 2012 and published as WO/2014/029421 on Feb. 27, 2014 (Inventor—Gasparyan et al) (6 pages).

International Preliminary Report on Patentability was mailed on Feb. 24, 2015 for International Application No. PCT/EP2012/066243 on Aug. 21, 2012 and published as WO/2014/029421 on Feb. 27, 2014 (Inventor—Gasparyan et al) (7 pages).

Preliminary Amendment was mailed Dec. 23, 2014 to the U.S. Patent and Trademark Office for U.S. Appl. No. 14/410,916, filed Dec. 23, 2014 and published as US 2015-0201877 A1 on Jul. 23, 2015 (Inventor—Gasparyan et al) (7 pages).

International Search Report was mailed on Apr. 3, 2013 for International Application No. PCT/EP2012/066251 which was filed on Aug. 21, 2012 and published as WO/2014/029424 on Feb. 27, 2014 (Inventor—Gasparyan et al) (4 pages).

Written Opinion was mailed on Mar. 18, 2013 for International Application No. PCT/EP2012/066251 which was filed on Aug. 21, 2012 and published as WO/2014/029424 on Feb. 27, 2014 (Inventor—Gasparyan et al) (6 pages).

International Preliminary Report on Patentability was mailed on Feb. 24, 2015 for International Application No. PCT/EP2012/066251 which was filed on Aug. 21, 2012 and published as WO/2014/029424 on Feb. 27, 2014 (Inventor—Gasparyan et al) (7 pages).

Preliminary Amendment was mailed Dec. 23, 2014 to the U.S. Patent and Trademark Office for U.S. Appl. No. 14/410,954, filed Jun. 25, 2012 and published as US-2015-0313630-A1 on Nov. 5, 2015 (Inventor—Gasparyan et al) (10 pages).

European Patent Office Communication Pursuant to Rules 161(1) and 162 EPC was mailed on Mar. 21, 2015 by the European Patent Office for EP Application No. 12761919.5, which was filed on Aug. 21, 2012 and published as 2887868 on Jul. 1, 2015 (Inventor—Gasparyan et al) (2 pages).

Response to European Patent Office Communication Pursuant to Rules 161(1) and 162 EPC was mailed on Oct. 2, 2015 to the European Patent Office for EP Application No. 12761919.5, which was filed on Aug. 21, 2012 and published as 2887868 on Jul. 1, 2015 (Inventor—Gasparyan et al) (2 pages).

European Patent Office Communication Pursuant to Rules 161(1) and 162 EPC was mailed on Mar. 27, 2015 by the European Patent Office for EP Application No. 12766389.6, which was filed on Aug. 21, 2012 and published as 2887889 on Jul. 1, 2015 (Inventor—Gasparyan et al) (2 pages).

Response to European Patent Office Communication Pursuant to Rules 161(1) and 162 EPC was mailed on Oct. 5, 2015 to the European Patent Office for EP Application No. 12766389.6, which was filed on Aug. 21, 2012 and published as 2887889 on Jul. 1, 2015 (Inventor—Gasparyan et al) (6 pages).

Requirement for Restriction or Election issued on Sep. 30, 2016, by the U.S. Patent and Trademark Office for U.S. Appl. No. 14/410,954, filed Jun. 25, 2012 and published as US-2015-0313630-A1 on Nov. 5, 2015 (Inventor—Gasparyn et al) (9 pages).

Non-Final Office Action was issued on Feb. 16, 2017, by the U.S. Patent and Trademark Office for U.S. Appl. No. 14/410,954, which was filed Jun. 25, 2015 and published as US 2015-0313630 A1 on Nov. 5, 2015 (Inventor—Gasparyan et al) (10 pages).

(56) References Cited

OTHER PUBLICATIONS

Requirement for Restriction/Election was issued on May 1, 2017, by the U.S. Patent and Trademark Office for U.S. Appl. No. 14/410,916, which was filed on Dec. 23, 2014 and published as US 2015-0201877 A1 on Jul. 23, 2015 (Inventor—Gasparyan et al) (9 Pages).

* cited by examiner

121

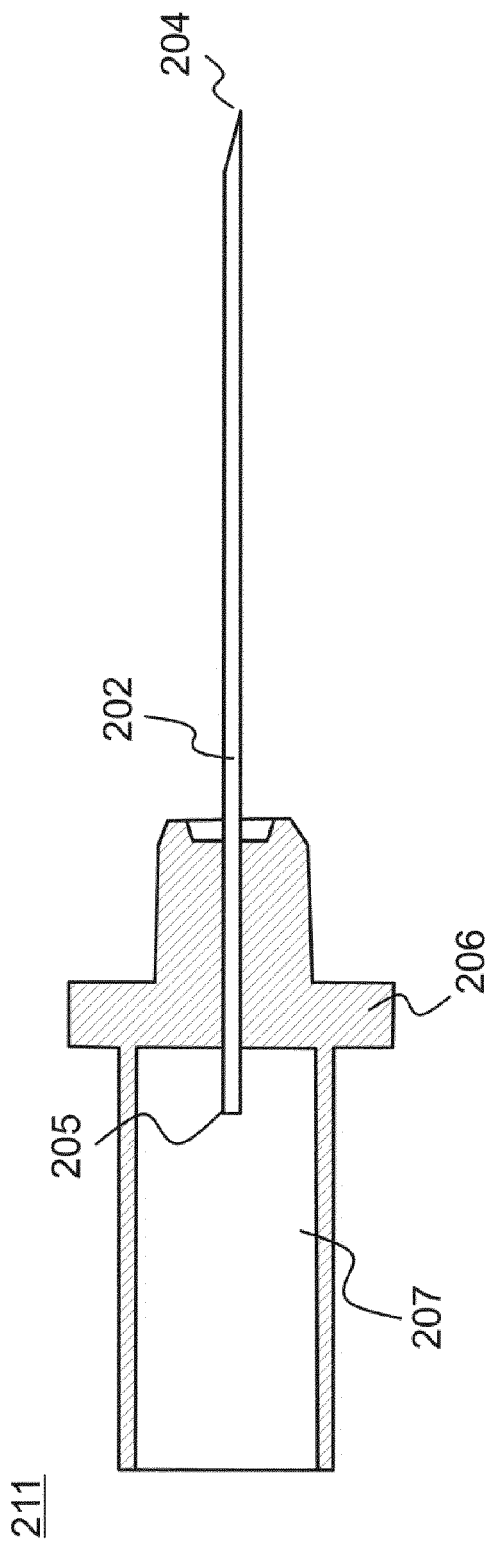
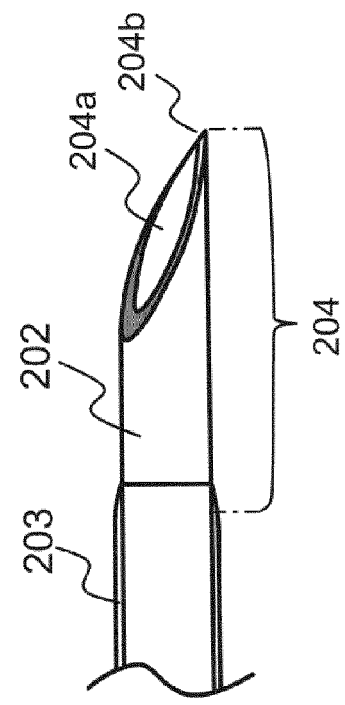
Figure 2B
Figure 2C

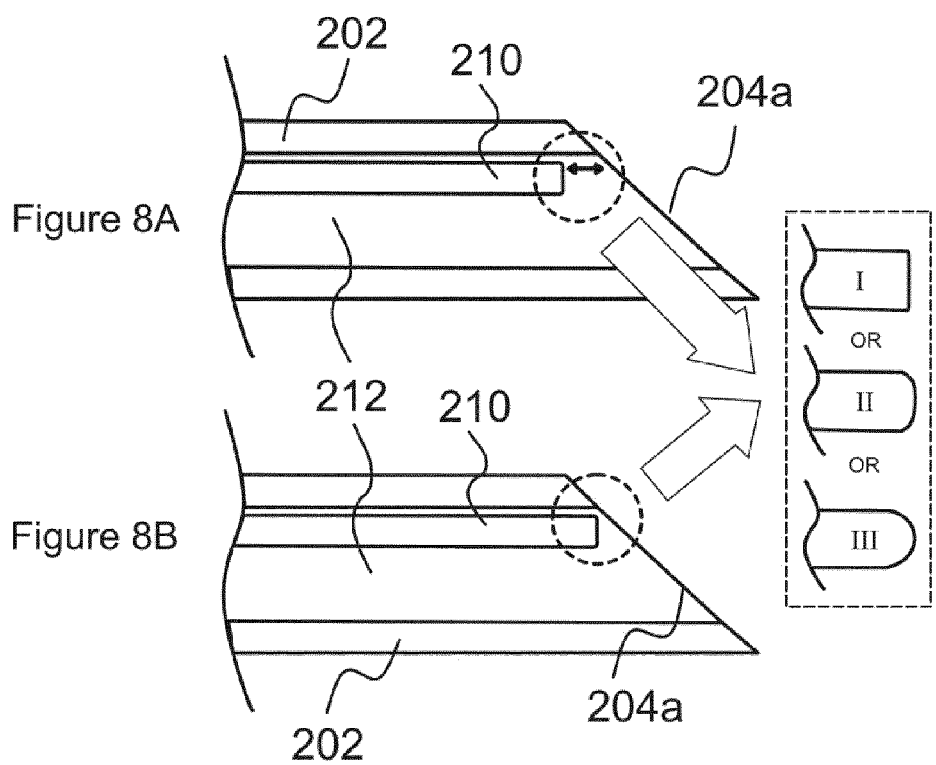
Figure 8A
Figure 8B
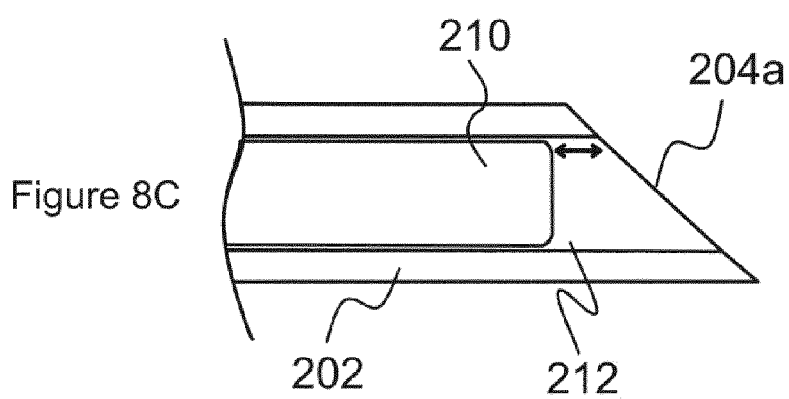
Figure 8C
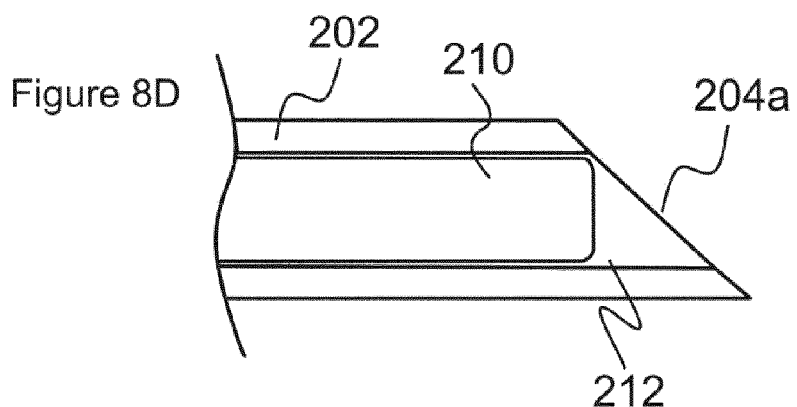
Figure 8D

INTRAVASCULAR CATHETER ASSEMBLY

CROSS-REFERENCE TO RELATED APPLICATIONS

The present application is a U.S. National Phase Application of International Application No. PCT/EP2012/066246, filed Aug. 21, 2012.

FIELD OF THE INVENTION

The present invention relates to medical intravascular catheter systems and in particular to intravascular catheter assemblies.

BACKGROUND

Intravascular catheter systems, such as peripheral intravenous catheters or central venous catheters, for example, are essential in modern medical practice. Catheter systems are commonly used for fluid infusion or withdrawal, or for monitoring various physiological parameters, such as blood pressure, pH and blood gas tensions. Catheter systems may be also used for introducing and locating probes, such as blood gas- or blood pressure probes.

Conventional method of placing the catheter into a blood vessel using over-the-needle technique comprises skin puncture with an introducer needle, moving the needle in surrounding tissues forward towards target blood vessel, puncturing the wall of a target blood vessel and pushing a catheter inside target blood vessel while removing a needle. In case of over-the-wire technique a guidewire is used prior to placement or insertion of the catheter inside of the blood vessel. An indication of a successful blood vessel puncture is a blood flow into a flashback chamber that is commonly visually observed. However, one of the major problems during venipuncture or arterial line placement is difficulty in determination of the exact position of a needle tip inside the skin relatively to a blood vessel. In most conventional systems venipuncture is performed based on the results of both visual observation and palpation of skin area to be punctured, and often a blood vessel is not located correctly on a first try. Also blood vessels, otherwise visible through the light skin may not be as well detectable through the dark skin. Another problem is that, an observation of blood flow to a flashback chamber is not always a reliable indicator of blood vessel's wall penetration. Some amount of blood may also appear in the flashback chamber whether the needle penetrates blood vessel throughout, thus ending up not in the lumen of the blood vessel, but in surrounding tissues. In case a clinician is not always able to recognize the fact of throughout penetration, catheter placement into an incorrectly punctured blood vessel may cause a permanent damage of a blood vessel. Hereto relates another problem of clinician might be unaware of a moment when to stop pushing the needle forward inside the blood vessel, which may also be the reason for damaging blood vessel from inside. In fact, correct positioning of a catheter system on any patient with small, deep, faulty or damaged veins is conjugated with aforesaid problems. All above mentioned problems become especially noticeable in case of emergency, ambulance and/or in children's hospitals.

Blood vessel entry indicator means for catheter systems, other than observation of blood flow into a flashback chamber, have been developed.

A device, producing sound signal upon entering blood vessel, is known from U.S. Pat. No. 5,954,701.

Blood vessel entry visual indicator, operating via inflating a mechanical part inside said device in response to blood pressure, is disclosed in U.S. Pat. No. 5,314,410.

US 2007/073160 discloses a light-guided catheter assembly with inside-out transcutaneous illumination and visualization of its placement through the skin and its application method.

The method thereof is based on a photochemical reaction, wherein an optical signal radiates back from fluorescenting molecules present in patient's blood stream and is further guided to a detector.

An intravenous puncture assembly with blood vessel location means based on visual detection of color change of crystalline material inside the needle hub is provided in U.S. Pat. No. 4,971,068.

U.S. Pat. No. 4,311,138 discloses an illuminated hypodermic catheter needle assembly adapted to emit light from its distal end to facilitate venipuncture under subdued lighting conditions. However, said device enables the needle to be seen through skin, while no indication of the detection of a successful blood vessel penetration is given. An indication of the correct position of the needle is provided by reflux of blood back through the needle, i.e. a clinician ends up with visual observation of blood flowing to a flashback chamber.

Blood visualization systems based on optical radiation absorption by hemoglobin are promising, but rather poorly developed. Devices known from previous patent publications are either rather complicated in use or have never been put into practice. However, the phenomena of absorption of optical radiation of certain wavelength by hemoglobin may be successfully implemented in medical devices intended for puncturing blood vessels. What is needed is to provide a fast, easy, accurate and consistent device for blood vessel puncture, capable of providing reliable indication of blood vessel entry other than visual observation of blood flow into a flashback chamber. It is further desirable that said device would not require any additional equipment, like e.g. detectors or goggles, in order to be easily applicable in emergency situations.

SUMMARY OF THE INVENTION

The objective of the invention is to alleviate above mentioned problems by implementing an intravascular catheter assembly with means for fast and accurate blood vessel localization, for the detection of an exact moment of intravascular penetration and for the recognition of a right instant to stop pushing the needle forward when the blood vessel is punctured, in accordance with the certain embodiments of the invention.

This objective is achieved by providing an intravascular assembly for catheterization to perform placement of arterial or venous catheters comprising a tubular introducer needle comprising a connection hub and a needle member, wherein the needle member has a lumen, a distal end and a proximal end. The assembly further comprises a light guide which has a distal end and a proximal end and extends along the lumen of the needle member, and an adapter, to which the light guide is fixed. The adapter can be provided with an interface for a light source or electronic module, comprising technically appropriate mechanical and electrical components. The term 'interface' may also refer in this disclosure to a particular technical element provided to pass light from one part to the other, which parts may be located at a distance from each other. The interface may thus comprise of a mechanical connection between elements or of a light guiding element.

The adapter is fixedly or releasably connected to the connection hub of the introducer needle.

The assembly further comprises a cannula tubing which surrounds at least a portion of the needle member.

The assembly further comprises at least one light source and an electronic module that is configured to power the light source(s).

In some embodiments the adapter is fixedly or releasably connected to the electronic module.

The provision of the adapter makes it possible to isolate the light source and the electronic module from the remaining components of the assembly. Unlike the prior art solutions, in which the light source is arranged in a flashback chamber and thus gets into contact with blood during use, the light source and the electronic module of the present invention, which are usually the more expensive components of the entire assembly, can be reused without a need for sterilization. This significantly reduces the costs associated with usage of the assembly, because the relatively cheap components, i.e. the tubular introducer needle, the cannula tubing and the adapter, to which the light guide is fixed, can be disposed of after use, while the more expensive components are reusable.

The light guide may be fixed inside the lumen of the needle member. In that case the introducer needle and the adapter may be packaged as a pre-assembled unit which will be completely disposed of after usage.

In some embodiments the light guide is received in the lumen of the needle member such that it is capable of sliding along the lumen if a tensile force is applied to one end of the light guide. Then the light guide will be inserted into the lumen of the needle member during the process of connecting the adapter to the connection hub of the introducer needle.

In some embodiments the connection hub of the introducer needle is provided with an inner chamber, in particular a flashback chamber, which is adapted to receive a proximal end of the needle member.

Introduction of the light guide into the lumen of the needle member from the proximal end thereof may be facilitated if the connection hub is provided with a flashback chamber having a body portion that is shaped as a funnel. The proximal end of the needle member of the introducer needle may then be integrated within the vertex of the funnel and terminates therein so as to allow a fast and accurate insertion of the light guide into the needle member via the connection hub.

In another embodiment the connection hub is provided with a flashback chamber. However, here the assembly comprises a separate member positioned inside the connection hub. The separate member is configured as a double sided funnel having two funnel bases pointing to opposite directions. The funnels comprise a central through-bore ending at apertures on both funnel bases. An inner diameter of the bore is adapted to allow free sliding of the light guide therethrough. The apertures on both bases of the funnel are coaxial with the proximal end of the needle member so as to allow a smooth insertion of the light guide into the needle member via the connection hub.

Irrespective whether the light guide is fixedly or slidingly received in the lumen of the needle member, the connection between the adapter and the connection hub and/or the electronic module should be liquid-tight. This ensures that no blood or other liquids get into contact with the light source and the electronic module.

In one embodiment at least 40% of light that contributes to the total light intensity emerging from the distal end of the light guide has a wavelength between 500 nm and 580 nm. This corresponds to a green color. Green light is particularly well absorbed by blood and the walls of blood vessels, and thus it may be used to visualize the moment when the tip of the needle member penetrates the blood vessel.

Additionally or alternatively, at least 40% of light that contributes to the total light intensity emerging from the distal end of the light guide has a wavelength between 600 nm and 800 nm. This corresponds to red light that may be utilized for visualization of a target blood vessel under the skin before the blood vessel is penetrated.

It is also possible to produce green and red light simultaneously. Then at least 75% of light that contributes to the total light intensity emerging from the distal end of the light guide may have a wavelength between 500 nm and 800 nm. If the tip of the needle member then penetrates the blood vessel, the green light is absorbed, and the visible color for an observer changes from yellow to red.

A similar effect can be achieved if the light source is capable of producing white light.

If light having different colors shall be produced, it may be necessary to use two separate light sources that are configured to be operated simultaneously and/or subsequently.

In one embodiment the lumen of the needle member has a minimal diameter d. The distal end of the light guide is stably arranged inside the lumen of the needle member, but spaced apart from the distal end of the needle member by a distance that is greater than d/5 and smaller than 5d, and preferably the distance is greater than d/2 and smaller than 2d, and still preferably the distance is greater than 0.1 mm and smaller than 20 mm. Such a retracted arrangement of the distal end of the light guide is particularly useful if large blood vessels shall be penetrated.

In other embodiments the catheter assembly comprises a pushing mechanism that is configured to move the light guide, upon actuation of the pushing mechanism by a user, along the lumen of the needle member between a projection position, in which the distal end of the light guide projects over the distal end of the needle member at least by a distance 2d, and a retracted position, in which the distal end of the light guide is spaced apart from the distal end of the needle member at least by a distance d/2, preferably by a distance 0.1 mm, wherein d is the minimal diameter of the lumen of the needle member. Then a better visualization can be achieved (in the retracted position) if large blood vessels shall be penetrated, and it is also possible, in the projecting (extended) position, to illuminate the blood vessel from its inside by pushing the light guide through the blood vessel. In the projected position light guide will act as a guide wire for easier placement of a catheter similar to that used in over-the-wire technique of placement of arterial or central venous catheters.

In the retracted position, a part of the light guide may be arranged in a folded configuration within a flashback chamber, which is provided in the connection hub, or an inner chamber provided in the adapter. In the projecting position, the light guide is then unfolded so that it projects over the distal end of the needle member.

Preferably the pushing mechanism is operable by a switch.

In some embodiments the catheter assembly comprises safety means for preventing a user of being wounded by the sharp distal end of the needle member. The safety means are configured as an automatic retraction/extension mechanism for the light guide comprising the adapter being configured as a two-unit member, which comprises an outer unit, which has a central aperture, and a central unit, which is positioned within the central aperture of the outer unit, wherein the central unit is configured to be movable within the aperture of the outer unit and is provided with a bore to receive the light guide, said bore being sealed liquid-tightly against the light guide. An operation of the automatic retraction/extension mechanism is based on automatic rotational and/or translational movement of the central unit within the aperture of the outer unit upon mounting or dismounting the introducer needle onto the electronic module or from the electronic module, respectively.

The safety means thus ensure that the light guide projects over the sharp tip of the needle member as long as the introducer needle is not mounted on the electronic module.

At an initial position, before mounting the introducer needle with the adapter onto the electronic module, the central unit may then be located at a most distal position within the aperture of the outer unit so that the light guide, which extends slidably along lumen of the needle member, projects out of the distal end of the needle member. The central unit may then be configured to rotationally and/or translationally shift backward within the aperture of the outer unit upon connection of the electronic module to the adapter. This action causes the light guide to retract inside the lumen of the needle member, thus allowing the user to perform catheterization. The central unit may further be configured to rotationally and/or translationally shift forward within the aperture of the outer unit upon disconnection of the electronic module from the adapter. This action causes the light guide again to extend out of the lumen of the needle member.

In some embodiments the adapter is manufactured from a material that is semi-transparent for visible light. In other embodiments the connection hub of the introducer needle is manufactured from a material that allows at least a portion of the light guide to be visible to an outside observer. This portion may be located between the adapter and a proximal end of the needle member. If light is emitted by a lateral surface area of the light guides, the connection hub of the introducer needle is illuminated if the light source is powered.

In some embodiments the connection hub is provided with a flashback chamber. The assembly is configured to visualize at least one of the following illumination events at the connection hub of the introducer needle upon blood flow inside the lumen of the needle member and further on into the flashback chamber of the introducer needle connection hub: illumination fading, changing illumination colour, illumination fading along with changing illumination colour.

In some embodiments the adapter has a textured outer surface.

In some embodiments the adapter comprises at least two adapter parts, defined as matching segments and hold together by suitable lock fittings.

In some embodiments the adapter comprises at least two adapter parts being sequentially connected or connectable to each other, wherein the first adapter part is connected or connectable with the connection hub of the introducer needle and the second adapter part is connected or connectable with the electronic module.

In another embodiment the adapter comprises at least two adapter parts being sequentially connected or connectable to each other, wherein the first adapter part is formed as an integral part with the connection hub of the introducer needle and the second adapter part is formed as connected or connectable with the electronic module.

In another embodiment the adapter comprises at least two adapter parts being sequentially connected or connectable to each other, wherein the first adapter part is connected or connectable with the connection hub of the introducer needle and the second adapter part forms an integral part with the electronic module.

In other embodiments an outer diameter of the adapter is larger than an outer diameter of the connection hub of the introducer needle.

A distal portion of the connection hub may be manufactured from a material which is semi-transparent or opaque for visible light.

According to another aspect of the invention, a intravascular catheter assembly is provided that comprises a tubular introducer needle comprising a connection hub and a needle member having a lumen, a distal end and a proximal end. The assembly further comprises a cannula tubing surrounding at least a portion of the needle member, an electronic module comprising at least one light source and also a light guide having a distal end and a proximal end extending along the lumen of the needle member. The proximal end of the light guide is optically coupled to the light source such that light emitted by the light source is capable of entering the light guide. The distal end of the light guide is arranged inside the lumen of the needle member, but spaced apart from the distal end of the needle member, by a distance that is greater than d/5 and smaller than 5d, and preferably by a distance that is greater than d/2 and smaller than 2d, still preferably by a distance that is greater than 0.1 mm and smaller than 20 mm, wherein d is the minimal diameter of the lumen (212) of the needle member (202).

According to a third aspect of the invention, a peripheral intravascular catheter assembly is provided which comprises a tubular introducer needle comprising a connection hub and a needle member having a lumen, a distal end and a proximal end. The assembly further comprises a cannula tubing surrounding at least a portion of the needle member, an electronic module comprising at least one light source, and a light guide having a distal end and a proximal end and extending along the lumen of the needle member. The proximal end of the light guide is optically coupled to the light source such that light emitted by the light source is capable of entering the light guide. The assembly further comprises a pushing mechanism that is configured to push the light guide, upon actuation of the pushing mechanism by a user, further through the lumen of the needle member such that the distal end of the light guide projects over the distal end of the needle member at least by a distance b, which may be greater than 2 mm and smaller than 20 mm.

In another aspect of the invention, a method for intracutaneous localization of the blood vessels, for the detection of an exact moment of the intravascular penetration and for safeguarding the blood vessel from being damaged from inside is provided.

In still another aspect of the invention, a fast and accurate method for placing a peripheral intravascular catheter and for performing at least initial stages of placement of central venous catheter into a blood vessel is provided.

The terms "peripheral intravascular assembly for catheterization" and "peripheral intravascular catheter" refer in this disclosure to the same device, namely to an assembly for performing catheterization procedure and placed into a peripheral blood vessel, i.e. blood vessel located not in the chest or abdomen and thus being most commonly accessed by intravascular methods.

The terms "assembly for performing central venous catheterization" and "central venous catheter" refer in this disclosure to the same device, namely to an assembly for performing catheterization procedure into a large veins, for example, veins in the neck (internal jugular vein), chest (subclavian vein or axillary vein) or groin (femoral vein).

The term "blood vessel" may in this disclosure be vastly equivalent to the term "vein", since peripheral veins are the most common access point for intravascular methods. To those skilled in art, however, it must be clear that the term "blood vessel" may also relate to arteries.

The term "light" refers in this disclosure to electromagnetic radiation including ultraviolet, visible and infrared light.

Different embodiments of the present invention will become apparent by consideration of the detailed description and accompanying drawings.

BRIEF DESCRIPTION OF THE DRAWINGS

FIG. 2B illustrates an introducer needle of the intravascular catheter assembly in accordance to the embodiments of the invention.

FIG. 2C illustrates a distal end of the intravascular catheter assembly of FIG. 2A.

FIG. 8A-D illustrate a catheter needle tip of an intravascular catheter assembly of the invention comprising a light guide in its lumen, wherein said light guide is provided in various configurations.

FIG. 15A shows a light guide in folded position and FIG. 15B shows a light guide in extended position, in accordance with some embodiment.

DETAILED DESCRIPTION OF THE EMBODIMENTS

Figure 1A:
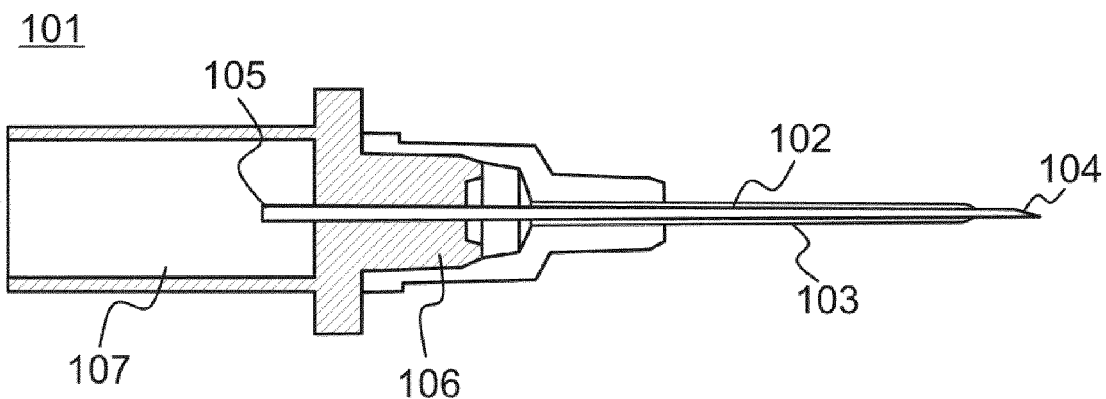
FIG. 1A illustrates a conventional peripheral intravascular catheter assembly.
Figure 1B:
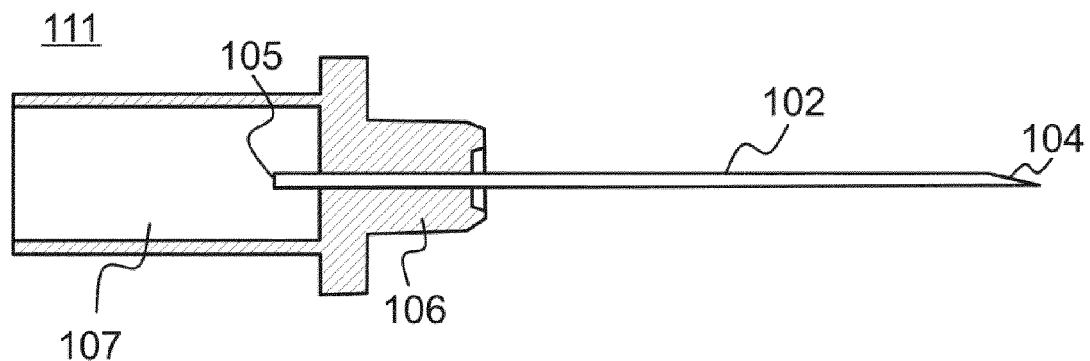
FIG. 1B illustrates an introducer needle of a conventional peripheral intravascular catheter assembly.

Detailed embodiments of the present invention are disclosed herein with the reference to accompanying drawings. The same reference characters are used throughout the drawings to refer the same members. Following citations are used for the members:

Prior Art:
101—intravascular catheter assembly;
111—introducer needle provided with a connection hub;
102—metallic needle member;
121—cannula;
103—cannula tubing;
104—insertion (distal) end of the needle member of the introducer needle;
105—chamber (proximal) end of the needle member of the introducer needle;
106—connection hub of the introducer needle;
107—flashback chamber formed by an inner space of the connection hub (106);
108—blood.
Present Disclosure:
201—intravascular catheter assembly in accordance with some embodiment of the invention;
211—introducer needle provided with a connection hub;

202—metallic needle member;
203—cannula tubing;
204—distal end of the needle member of the introducer needle;
204a—a blood entry aperture at the distal end 204;
204b—tip (as a sharp point) of the needle member of the introducer needle;
205—proximal end of the needle member of the introducer needle;
206—introducer needle connection hub;
207—flashback chamber formed by an inner space of the introducer needle connection hub 206;
208—blood;
209—adapter;
209D—adapter distal connection hub;
209P—adapter proximal connection hub;
221—adapter bore;
222a, 222b—lock fittings for the multi-segment adapter;
219—outer unit of the two-unit adapter (the body);
229—inner (central) unit of the two-unit adapter;
219a—bore in the two-unit adapter outer unit (219);
229a—bore in the two-unit adapter inner unit (229);
210—light guide;
212—introducer needle lumen;
213—adapter screw thread;
301—an electronic module;
302—electronic module connection hub;
303—contacts;
312—light source;
312a and 312b—first and second light sources, respectively;
314—light converging device;
316—case for non-releasable adapter
320—insert for a flashback chamber (207) of the introducer needle connection hub (206);
501—light emitted from the distal end of the introducer needle;
601—space in the distal end of the catheter needle, filled with blood, is of particular importance for small and thin blood vessels;
701—a pushing mechanism;
702—a switch for releasing an extendable light guide.

Figure 1C:
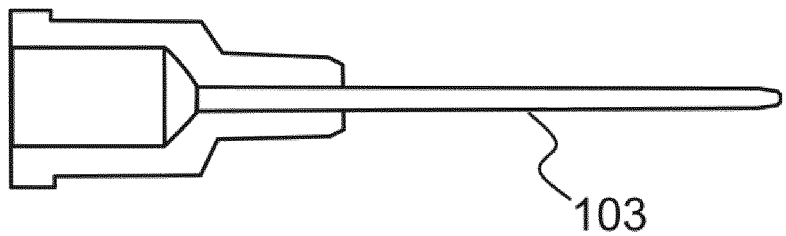
FIG. 1C illustrates a cannula of a conventional peripheral intravascular catheter assembly.
Figure 1D:
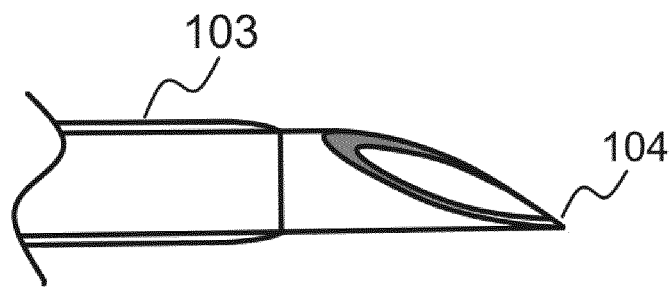
FIG. 1D illustrates a distal end of conventional peripheral intravascular catheter assembly.

A conventional peripheral intravascular catheter assembly is illustrated by FIGS. 1A-1E (prior art). FIG. 1A shows a catheter assembly 101, which assembly comprises an introducer needle 111 (FIG. 1B) onto which an over-the-needle flexible plastic cannula 121 (FIG. 1C) with cannula tubing 103 is mounted. Introducer needle 111 (FIG. 1B) thus comprises a metallic needle member 102 and a connection hub 106, which hollow interior forms a flashback chamber 107. Introducer needle member 102 is thus provided with a sharp insertion end 104 (FIG. 1D), referred herein as a distal end or the tip of the needle, and with a chamber end 105, referred herein as a proximal end. FIG. 1C shows a plastic cannula 121, comprising a flexible cannula tubing 103, which is normally being left in a blood vessel after venipuncture. Conventional intravascular catheter assemblies may also include additional technical features, such as Luer lock plug, additional injection port with a protective cap, wings, needle grip and/or safety device.

Figure 1E:
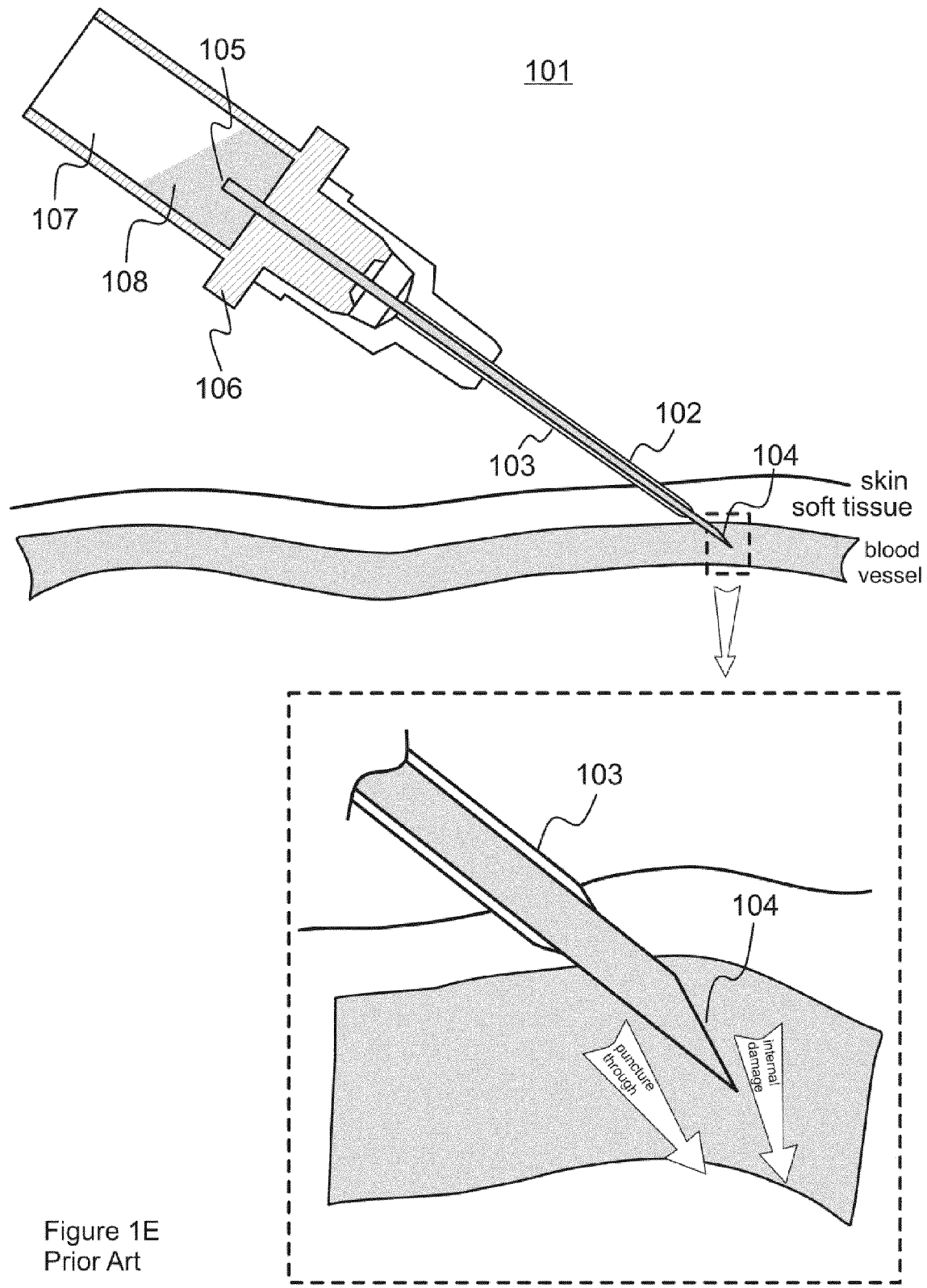
FIG. 1E illustrates a process of an introduction of a conventional peripheral intravascular catheter assembly into a blood vessel.

A conventional process of an introduction of a intravascular catheter into a blood vessel, that blood vessel may be a vein, for example, involves several steps, disclosed further by an example of FIG. 1E (prior art). FIG. 1E thus illustrates an exemplary catheter assembly 101 at the moment of the insertion of the introducer needle into a blood vessel, e.g. a vein, through skin and tissues. At the moment needle member 102 penetrates the vein, blood 108 flows into a flashback chamber 107, thus confirming an event of needle vein entry. As soon as distal end 104 of the introducer needle is inside the vein, flexible cannula tubing 103 may be pushed forward and metallic needle member 102 may be removed from the vein. After securing cannula tubing 103 to skin, cannula 121 may be connected to an intravascular line or other system. Thus, in conventional systems the event of entering a blood vessel is represented by observing blood flow into a flashback chamber of the catheter assembly.

The major disadvantage of the known method is that, the moment of venipuncture may be detected only by visual monitoring of blood appearance in a flashback chamber. In addition, the location of a blood vessel under skin is mostly performed visually and/or by means of palpation. By means of a conventional system, disclosed above, it is impossible to assure whether blood vessel is punctured correct, i.e. whether the needle tip entered the lumen of the blood vessel and is positioned correctly therein. Situations, when the needle punctures blood vessel throughout and hits surrounding soft tissue afterwards, allowing however some amount of blood to flow into a flashback chamber, are thus undetectable. Improperly placed catheter may further cause damages to blood vessel walls and make a patient to suffer unnecessary stress and complications. In cases of emergency and/or performing venipuncture on kids a fast and correct placement of the catheter system inside the blood vessel is of particular importance.

An intravascular assembly for catheterization in accordance with the embodiments of present invention is configured as a unit, comprising an introducer needle and an adapter to which a light guide is fixed or mounted. The light guide is provided as a single optical fiber or a bundle of fiber optics and is arranged to extend substantially from the light source to the distal end of the introducer needle, preferably terminating within the introducer needle. The introducer needle is connectable or connected to the adapter. The connection may be realized as permanent or releasable. The assembly may be completely or partly disposable; in latter case only an introducer needle with a light guide are disposable. The assembly may be further provided with at least one light source and an electronic module configured to power the light source(s). The electronic module may be implemented as a multiple use device. Connection between an introducer needle, an adapter and electronic module may be realized as releasable or permanent between at least two these elements.

Figure 2A:
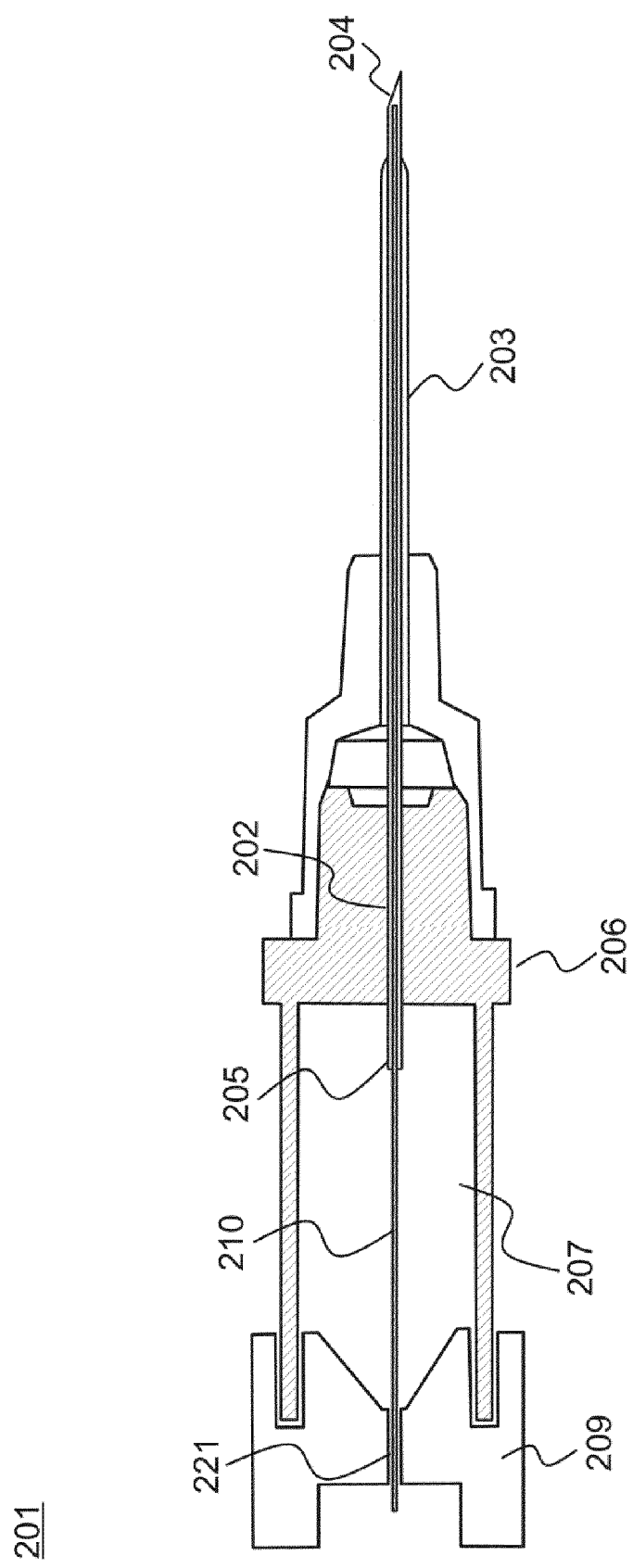
FIG. 2A illustrates an intravascular catheter assembly of the present invention in accordance to one embodiment.

The intravascular assembly for catheterization 201 in accordance with some embodiments is illustrated by FIG. 2A. All components of the assembly 201 are preferably provided as a disposable, vacuum-packed assembled unit; however, variations are possible and are disclosed below. Catheter assembly 201 comprises an introducer needle 211 (illustrated by FIG. 2B), said introducer needle in turn comprising a metallic needle member 202 and a connection hub 206. Needle member 202 may be any needle provided suitable for catheterization and has a lumen, a sharp tip 204b with an intended function to penetrate skin and to enter the lumen of the target blood vessel, as well as a proximal end 205 terminating in a plastic inner chamber 207. For clarity purposes distal end of the needle member 202 is defined in this disclosure as 204 at FIG. 2C, namely as distance between the tip 204b and that part of the distal end of the catheter tubing that forms a cone. An opening at the distal end of the introducer needle and, in particular, the surface area profile of said opening is designated herein as blood entry aperture 204a (FIG. 2C). A surface area profile of the opening 204a is conventionally represented by a regular circle or a regular ellipse; however other profiles are not excluded. An inner chamber, preferably a flashback chamber 207 is formed by a hollow interior of the connection hub 206. In some embodiment the inner chamber is a flashback chamber. The introducer needle 211 may also be a so called butterfly needle, for example, which is usually provided with a pair of wings and with plastic tubing arranged between the metallic needle member and a flashback chamber normally used for peripheral intravascular catheterizations. FIG. 2C illustrates a distal end 204 of the needle member 202 of the introducer needle 211 (FIG. 2B).

Assembly 201 further comprises a light guide 210, represented by a single optical fiber or a bundle of fiber optics, for example, and an adapter 209, to which the light guide 210 is fixed or mounted. Adapter 209 is provided as a unit whose outer diameter preferably exceeds an outer diameter of the connection hub 206 of the introducer needle 211. Adapter 209 is further provided with a bore 221 within a body thereof, adapted to receive the proximal end of the light guide 210.

The adapter 209 is provided with an interface for a light source and/or electronic module (not shown), in accordance to some embodiments. For those skilled in art it is obvious, that interface for the light source may comprise any suitable and/or technically appropriate mechanical and/or electrical components for being able to connect suitable light source to the adapter 209. The adapter 209 is configured as a unit provided with connection means to the electronic or power module, as disclosed below.

The light guide 210 is adapted to extend substantially from the light source interface to the distal end of the introducer needle, thus extending at least partly through adapter bore 221, where it is fixed, through the flashback chamber 207 and through the lumen of the needle member 202. The light guide may be implemented to be withdrawable from the introducer needle by means of pulling the adapter 209 to which the light guide is fixed or mounted.

In some embodiments the light guide 210 is fixed or mounted at a close vicinity to the adapter 209.

In some embodiments assembly 201 further comprises a plastic cannula provided with flexible cannula tubing 203 (FIGS. 2A, 2C) which cannula tubing is adapted to surround at least a portion of the needle member 202.

Figure 2D:
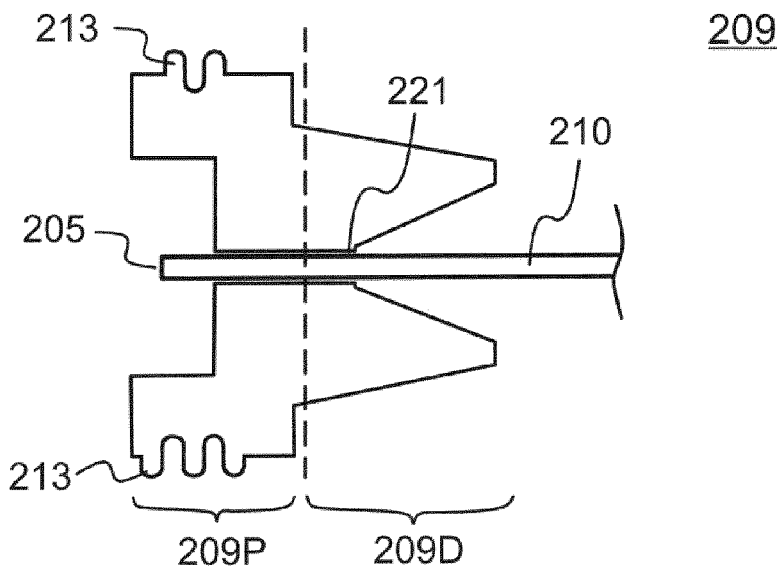
FIGS. 2D and 2E illustrate an adapter of the intravascular catheter assembly in accordance to some embodiments.
Figure 2E:
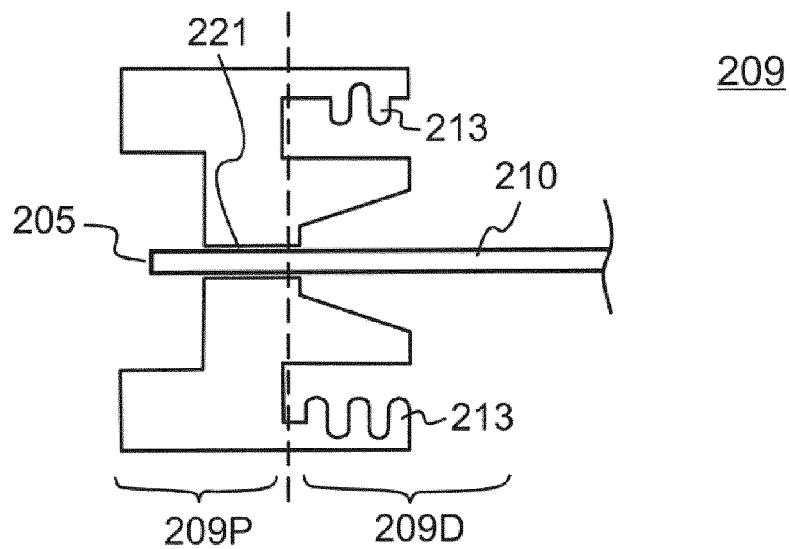

FIGS. 2D and 2E illustrate different types of suitable adapters 209 preferably but not exclusively provided as various modifications of Luer-adapter. FIG. 2D shows a so called "Luer-slip" and FIG. 2E a so called "Luer-lock". Luer-type adapter represent common prior art and are not disclosed further in this document. Adapters of FIGS. 2D and 2E are provided with distal and proximal ends or sides, referred herein as distal and proximal connection hubs (209D and 209P, respectively) and the bore 221 in the middle. Distal connection hub 209D is provided for coupling the adapter 209 to the connection hub 206 of the introducer needle 211. The coupling is preferably releasable; however a permanent connection is not excluded. Distal connection hub 209D is preferably configured to be compatible with conventional introducer needles. Proximal connection hub 209P is provided for enabling adapter coupling to an electronic module, as disclosed below. Said connection may be fixed or releasable. Depending on modification, a screw thread 213 is provided either on proximal or distal connection hubs. The preferable configuration of the catheter assembly comprises the adapter 209 of FIG. 2D, and said adapter configuration will be taken as an example for further figures disclosed in this document. Luer type of the adapter is only exemplary and is not to limit the invention, so that other types of the adapters may also be utilized.

Figure 2F:
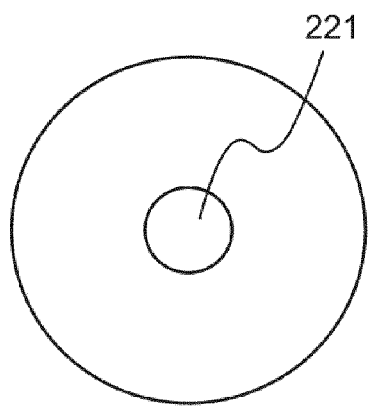
FIG. 2F illustrates a vertical cross-section of the exemplary adapter.

FIG. 2F illustrates a profile for vertical cross-section of simplest exemplary adapter 209 with a bore 221.

Figure 2G:
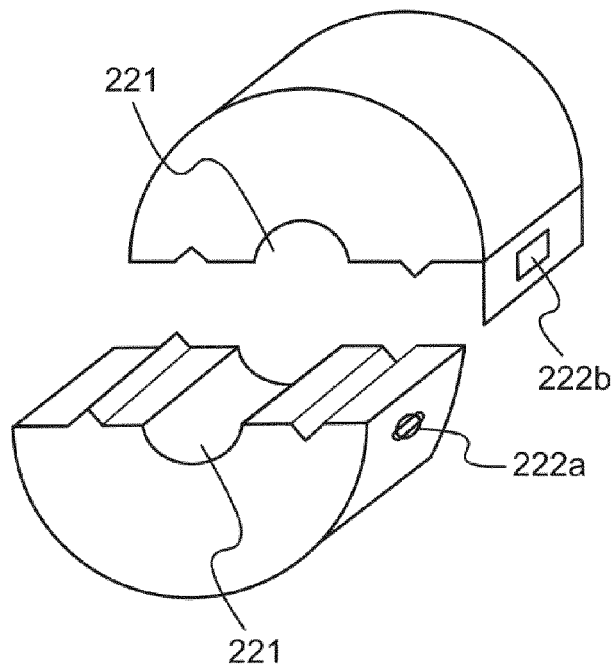
FIG. 2G illustrates the adapter in accordance with some embodiments, wherein the adapter is manufactured from two symmetrical segments of equal size cut along the adapter's horizontal axis and hold together by suitable lock fittings.
Figure 2H:
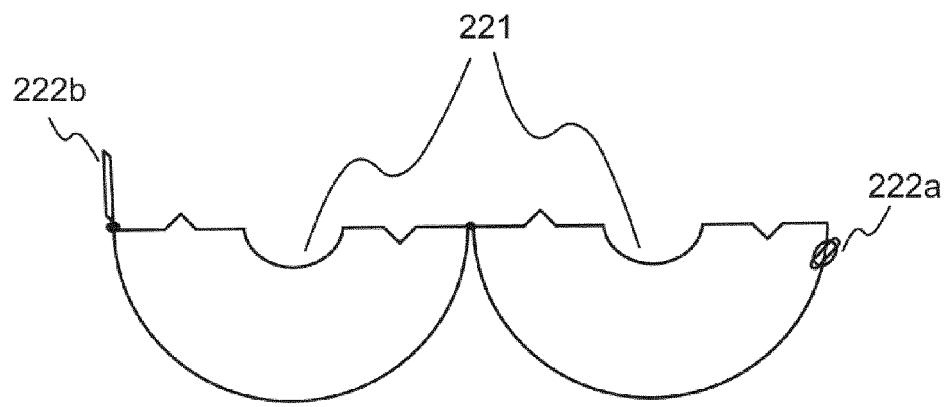
FIG. 2H shows a side profile of the adapter of FIG. 2G in unlocked position.

In accordance with some embodiment, the adapter 209 may be manufactured as a multi-part piece. FIGS. 2G and 2H thus illustrate a two-part adapter, whose parts are defined as matching segments cut along the adapter's horizontal axis and hold together by suitable lock fittings 222. Adapter segments join together by means of matching grooves and projections arranged on the connecting surfaces of the segments (FIGS. 2G, 2H). Suitable lock fittings may be that of a snap type (222a, 222b), for example. In case of two-segment adapter the segments are connected in between by a pivot connection, said connection located at the adapter side opposite to the of lock fittings 222. The amount of segments is not limited within the borders of technical feasibility.

In accordance with some embodiment, the adapter 209 is preferably manufactured from a material which is at least substantially semi-transparent for visible light.

In accordance to some embodiments, the assembly for catheterization 201 may be provided with at least one light source and an electronic or power module, configured to power said light source(s).

Figure 3A:
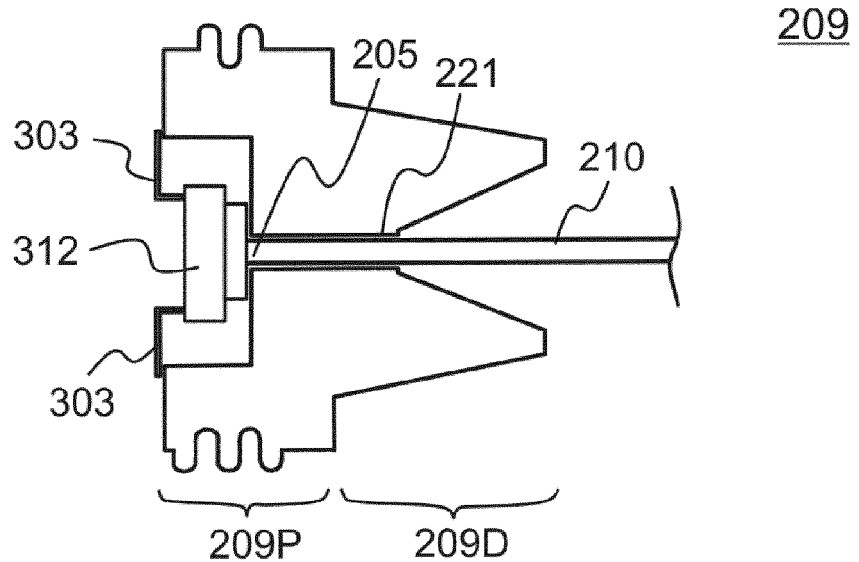
FIG. 3A illustrates a light source arrangement in single unit adapter in accordance with one embodiment.
Figure 3B:
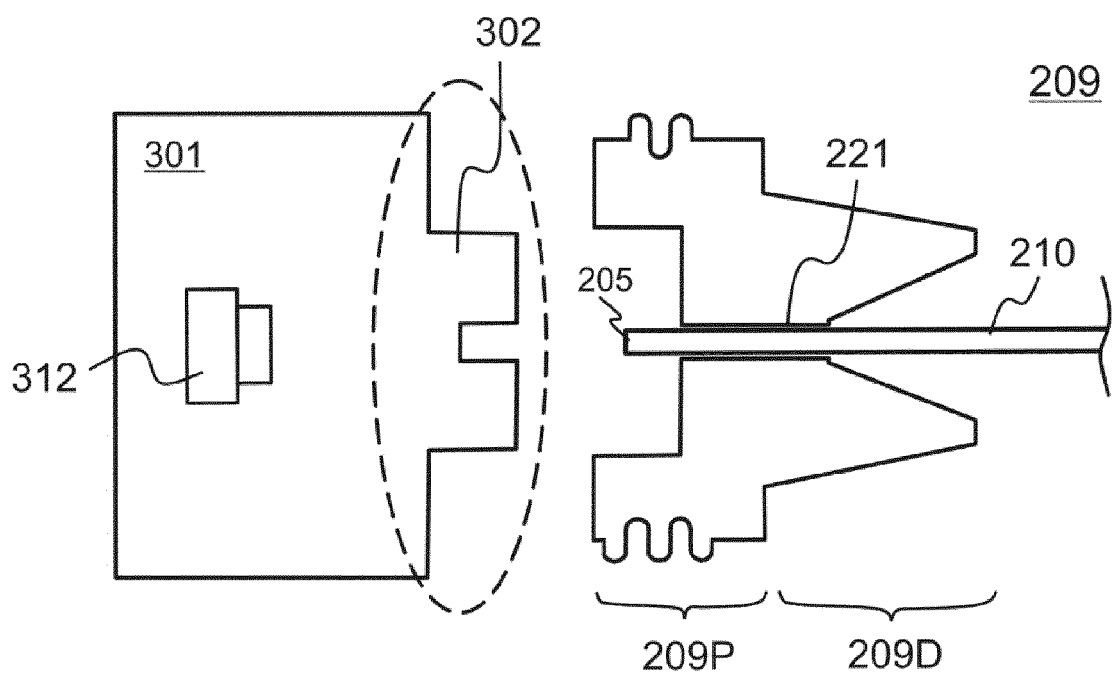
FIG. 3B illustrates a light source arrangement in single unit adapter in accordance with some other embodiment.

FIGS. 3A and 3B illustrate a suitable position of the light source 312 with respect to the adapter 209, which contribute to some embodiments of the invention. FIG. 3A illustrates one embodiment, wherein the adapter 209 accommodates the light source 312 in its proximal connection hub 209P. Light source 312 may be permanently secured in the proximal connection hub 209P by gluing, for example. However, the light source may also be releasably fixed and be held therein by means of electric contacts 303, for example. It is perfectly clear to those skilled in art that a method of securing the light source 312 in the proximal connection hub 209P may vary as long as the aim to bring the light source close to the proximal end of a light guide 210 is accomplished.

Adapter bore 221 is water-tightly sealed in order to prevent any fluid possibly reach the light source 312. In accordance with this embodiment, the proximal end of a light guide 210 is sealed within the bore of an adapter (FIG. 3A). The electronic module 301 (not on the figure) comprises an energy source for light source 312, such as a battery and the like.

FIG. 3B illustrates another embodiment of the invention, wherein the light source 312 is accommodated within the electronic module 301. The electronic module 301 is provided with a connection hub 302 (dashed circle), compatible with the proximal connection hub 209P of the adapter 209. The releasable connection may be implemented by any technically suitable way, like click-connection, screw-in and the like. Again, the proximal end of the light guide 210 is water-tightly sealed within the adapter bore 221 in order to prevent any fluid to possibly contact electric connections between the adapter 209 and the electronic module 301.

The adapter 209 may be additionally provided with a venting mechanism, preferably configured as an aperture within an adapter wall at least partially sealed by a porous filter-like member. The purpose of said venting mechanism is to allow air escape from the flashback chamber 207 to ambient surroundings at the same time preventing blood outflow thereto. Alternatively, but not exclusively, said venting mechanism can be placed into the wall of the connection hub 206 that forms a flashback chamber 207 of the introducer needle. Other possible embodiments for providing means for air escape from the flashback chamber 207 may include channels in the distal connection hub 209D of the adapter or similar.

Figure 4A:
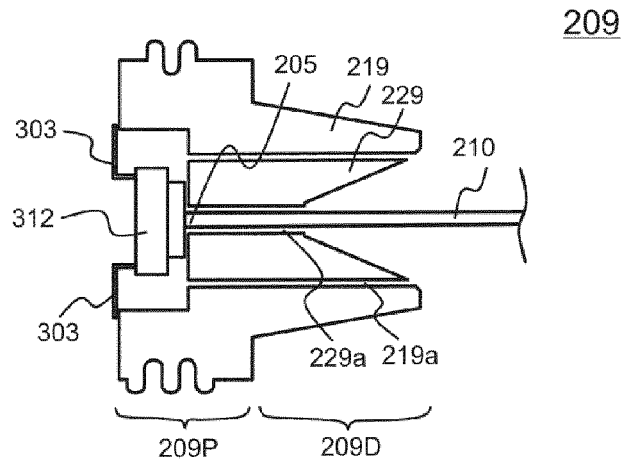
FIG. 4A illustrates a light source arrangement in two-unit adapter accordance with one embodiment.
Figure 4B:
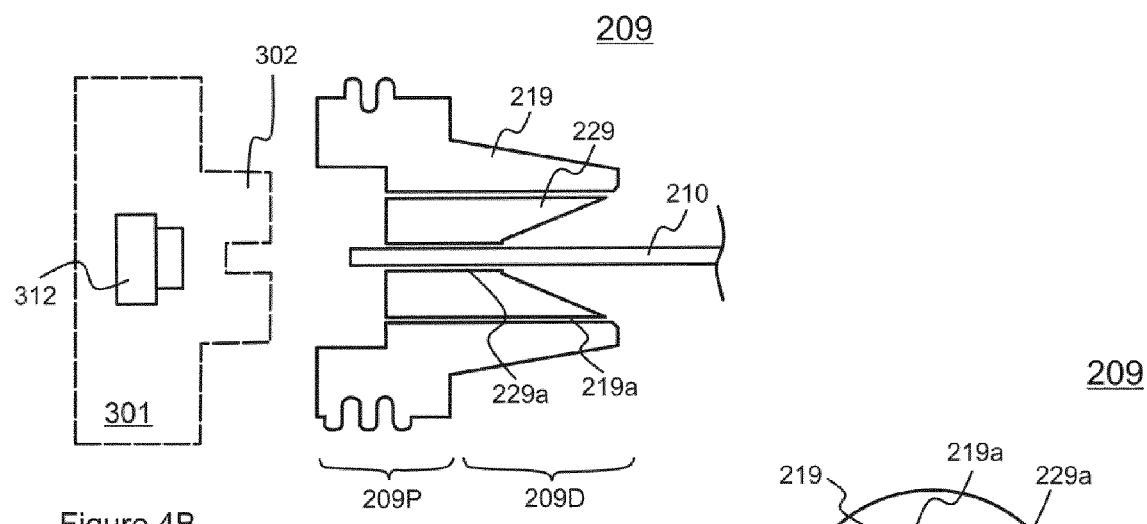
FIG. 4B illustrates a light source arrangement in two-unit adapter in accordance with some other embodiment.

FIGS. 4A and 4B illustrate a modified version of the adapter 209 in accordance with disclosed above arrangement. In accordance with this embodiment, the adapter 209 of the catheter assembly is configured as a two-unit member comprising an outer unit (the body) and an inner unit (central unit). Adapter body 219 is thus provided with a bore 219a, in which bore the central unit 229 is positioned. The central unit 229 is provided with a bore 229a adapted to receive the light guide 210 in the same manner as bore 221 of one-piece adapter described further above. Both units 219 and 229 have cylindrical shapes (FIG. 4C, crosscut), however, shape and form of said units is generally dependent on adapter design and does not limit the invention. The central unit 229 is configured to be capable of performing rotational and/or translational movements within a bore 219a of the outer unit, as further disclosed. FIG. 4A illustrates an embodiment with a light source 312 incorporated within an adapter, with the central unit 229 in operating position, as disclosed further.

FIG. 4B illustrates a two-unit adapter configuration in accordance with an embodiment, in which the light source 312 is accommodated within the electronic module 301, as this has been previously described.

Figure 4C:
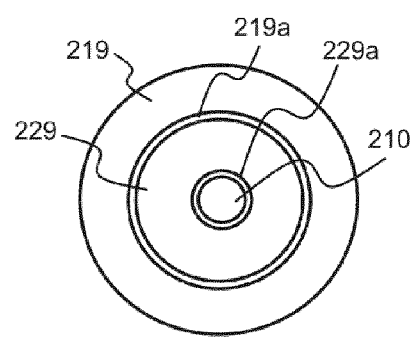
FIG. 4C illustrates a cross-section cut of a two-unit adapter of FIGS. 4A and 4B.

The catheter assembly, in accordance with the embodiments shown in FIGS. 4A to 4C, is provided with additional safety means for preventing the user of being wounded by a tip of an introducer needle. Said safety means is configured as an automatic retraction-extension mechanism for the light guide. The operation is based on automatic rotational and/or translational movement of the central unit 229 within the bore 229a of the outer unit 219 upon mounting an introducer needle 211 onto the electronic module 301 and upon dismounting therefrom. The mechanism is adjusted to operate essentially as disclosed in the following:

An "initial position" refers herein to a catheter assembly state, wherein the adapter 209 is disconnected from the electronic module 301. In the initial position the central unit 229 is shifted to the most distal position within the bore 219a of the outer unit 219, thus causing the light guide 210 to extend out from the lumen of the needle member 202 of the introducer needle 211 at the distal end 204 thereof. The light guide 210 extends e.g. few millimeters out of the tip of the needle member prior to mounting the introducer needle 211 and the electronic module 301, thus providing protection from accidental pricking fingers by the sharp needle tip, as well as preventing puncture of skin. In other words, in an absence of the electronic module one cannot puncture the skin.

The central unit 229 is configured to be displaceable within the outer unit 219. The central unit 229 is adjusted to automatically rotationally and/or translationally shift backward within the bore 219a of the outer unit 219 upon connection of the electronic module 301 to the proximal connection hub 209P of the two-unit adapter 209. This shifting movement causes the light guide 210 to retract inside the lumen of the needle member 202 of the introducer needle 211, thus leaving the sharp needle tip unobstructed and allowing the user to perform catheterization and/or other necessary actions.

The process is repeated the other way round upon dismounting the introducer needle 211 from the electronic module 301. The electronic module's disconnection triggers the central unit 229 to perform a rotational and/or translational shift forward within the bore 219a of the outer unit body 219, thus releasing the light guide 210 and allowing it to extend again out of the lumen of the needle member 202 of the introducer needle 211 to the initial position. This step is intended to protect the user from accidental wounding by a tip of the used needle.

Figure 5A:
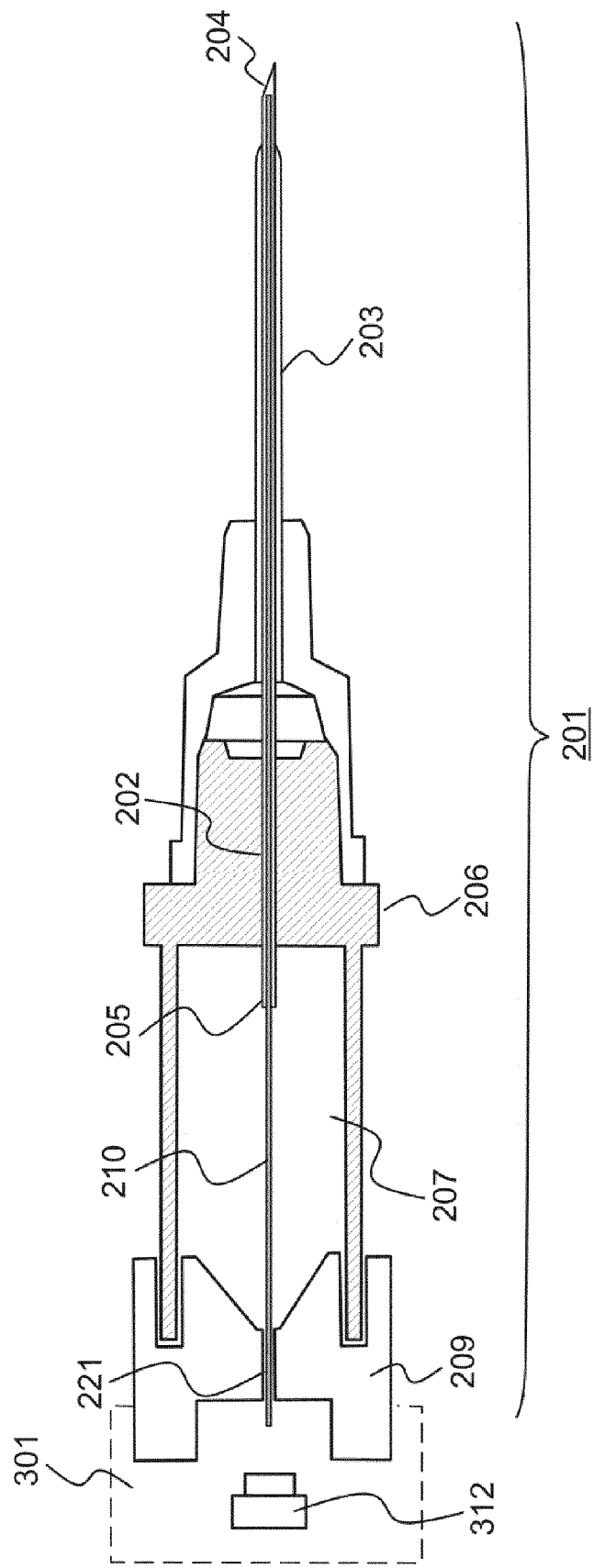
FIG. 5A illustrate an intravascular catheter assembly of FIG. 2A provided with an electronic module device in accordance to one embodiment.

FIG. 5A illustrates the assembly for catheterization 201 in accordance to some embodiments, wherein the assembly 201 is provided with an electronic module 301, connected to the adapter 209. Connection between elements 301 and 209 may be permanently fixed or releasable. FIG. 5A shows a position of the light source 312 inside the electronic module 301.

Figure 5B:
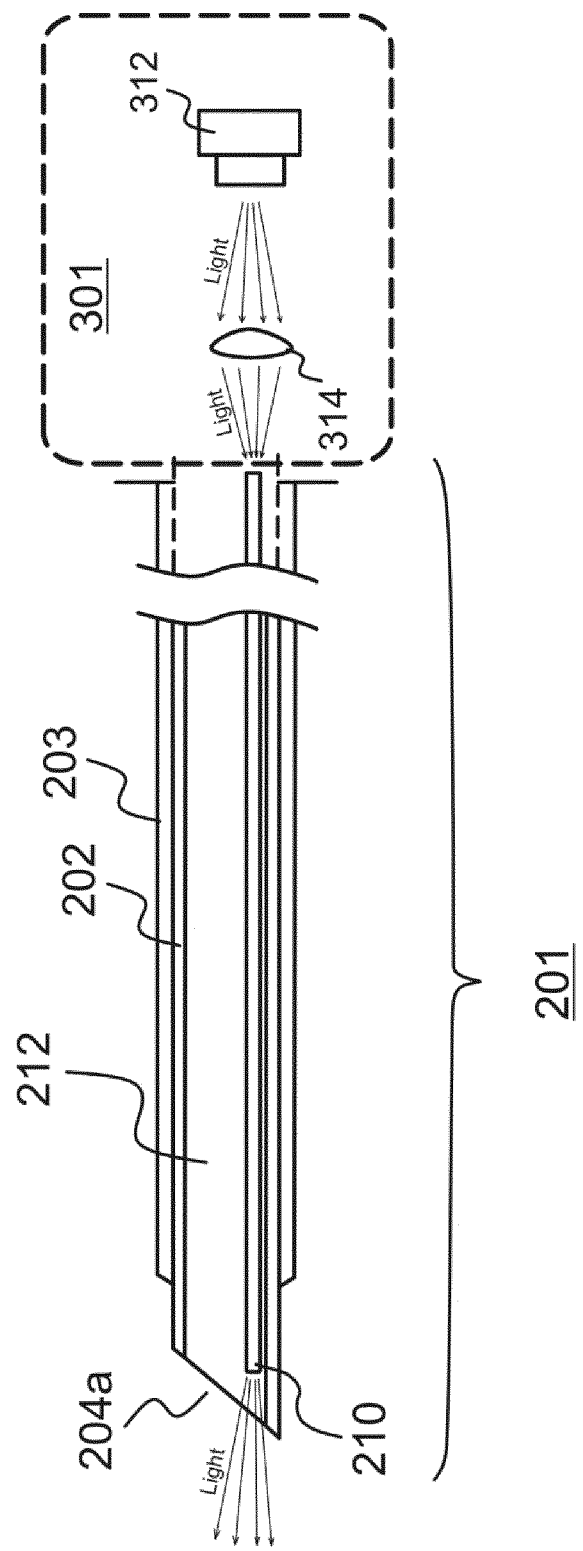
FIG. 5B schematically illustrates in more detail an intravascular catheter assembly connected to an electronic module device, in accordance to one embodiment.

FIG. 5B illustrates the assembly 201 provided with the electronic module 301 of FIG. 5A in more details. The light guide 210 is arranged inside the lumen 212 of the needle member 202 of the introducer needle 211 to be connected to the electronic module 301 via the adapter (not shown). The light guide 210 is stably positioned within the lumen 212 of the needle member, which stability is achieved by fixation of the light guide 210 by the adapter 209.

This embodiment illustrated the configuration, wherein the electronic module 301 is provided as a multiple use unit, whereas the assembly 201 is disposable.

The light guide 210 is adapted to receive light (FIG. 5B, shown by arrows) originating from the light source 312. The light guide 210 may be formed by a single optical fiber, a fiber optics bundle or any other suitable light transmitting means. The electronic module 301 of this embodiment comprises, in addition to the light source 312, also a light converging means 314 such as lens, for example, as well as an energy source and various electronic components and switches (not shown). An exemplary switch may be configured as an on-off switch, implemented, for example, as a manually operated pushbutton switch, a lever-actuated switch, a rotational switch, a slide switch or any other suitable type of an on-off mechanism capable of providing a control over an on-off state of an electronic module and/or an amount of emitted light. An exemplary switch may be configured to include additional usability and laser safety features and preferably implemented to be activated upon mounting the adapter onto the electronic module 301, and inactivated upon dismounting the blood collection needle from the tube holder.

Figure 6A:
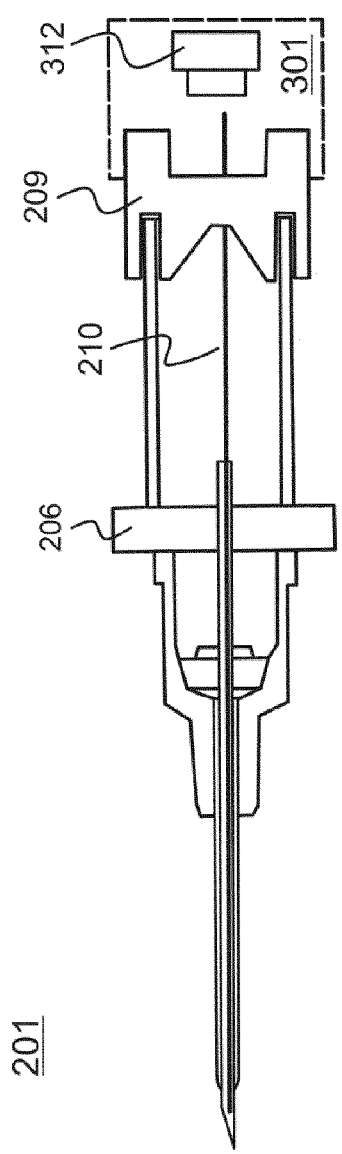
FIG. 6A-D illustrates additional embodiments of an intravascular catheter assembly of the invention.
Figure 6B:
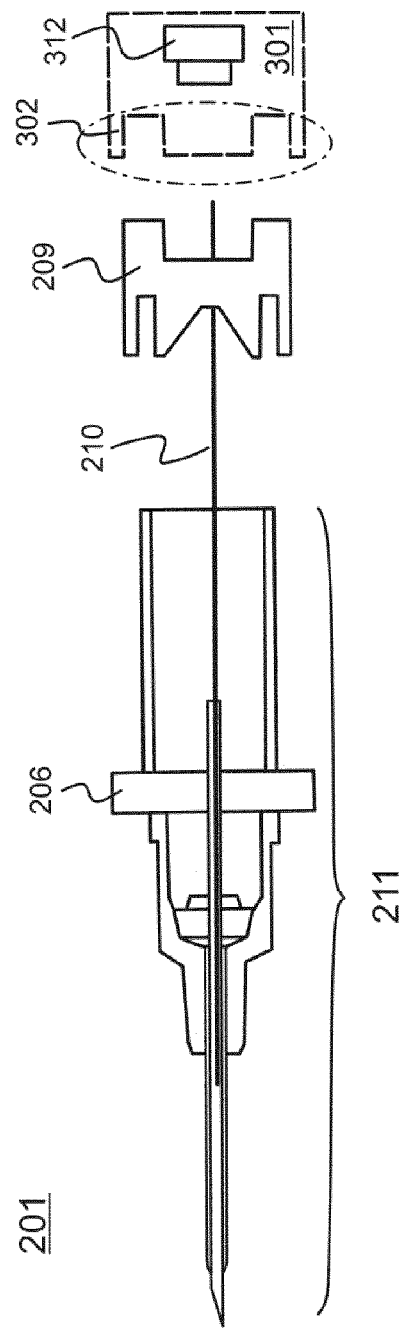

Additional configurations of a peripheral intravascular assembly for catheterization provided with the electronic module 301 are shown on FIGS. 6A-D. FIGS. 6A and 6B thus illustrate the configuration with an adapter that is connected both to the introducer needle 211 and to the electronic module 301. The connection between elements 211, 209 and 301 may either be fixed or releasable in the following way. In some embodiments the connection between the adapter 209 and the electronic module 301 may be either permanently fixed or releasable. In other embodiments the connection between the adapter 209 and the introducer needle 211 may also be either permanently fixed or releasable. In additional embodiments the connection between the needle member 202 and the adapter 209 may also be provided as permanent or releasable. Furthermore, in some embodiments elements 211, 209 and 301 may comprise a monolithic structure and be provided as one integral functional unit.

FIG. 6A shows the catheter assembly 201 in an assembled ready-to-use configuration. Since the light guide 210 is slidingly received in the needle member, but fixedly sealed within the adapter bore as disclosed above, the adapter 209 may be disconnected from the electronic module 301 so that the light guide 210 is pulled out of the introducer needle 211.

FIG. 6B shows adapter 209 disconnected from the electronic module 301 and from the introducer needle 211, with the light guide 210 partly pulled out of the connection hub 206 of the introducer needle 211. The main benefit of such an arrangement is the possibility of disconnecting the introducer needle from the adapter 209 and remove light guide from the lumen of the introducer needle any time in case of low battery and using the introducer needle 211 and therefore the catheter assembly in a conventional way. Here again the electronic module 301 is preferably provided as a multiple use device.

Figure 6C:
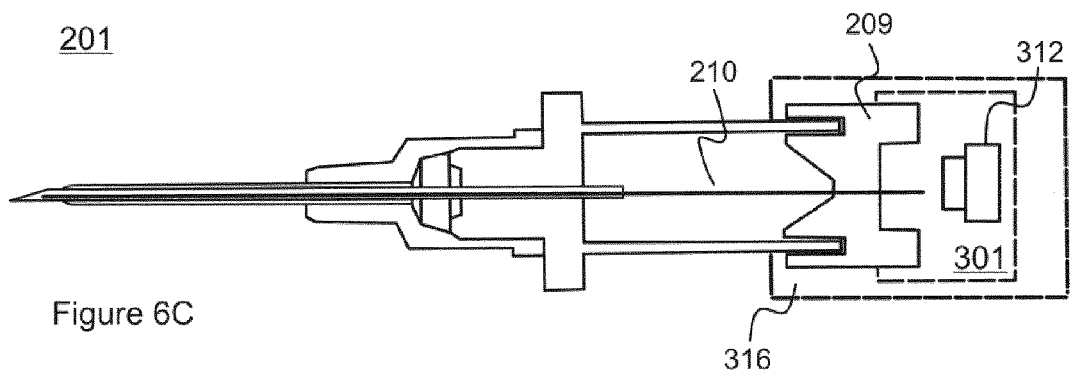

A catheter assembly 201 in an all-in-one configuration is shown in FIG. 6C. This configuration refers to a device in which all components are integrated, i.e. the connections between the components are not releasable. The whole device is thus disposable. In that case a proximal part of an introducer needle 211, the adapter 209 and the electronic module 301 are enclosed within a casing 316.

Figure 6D:
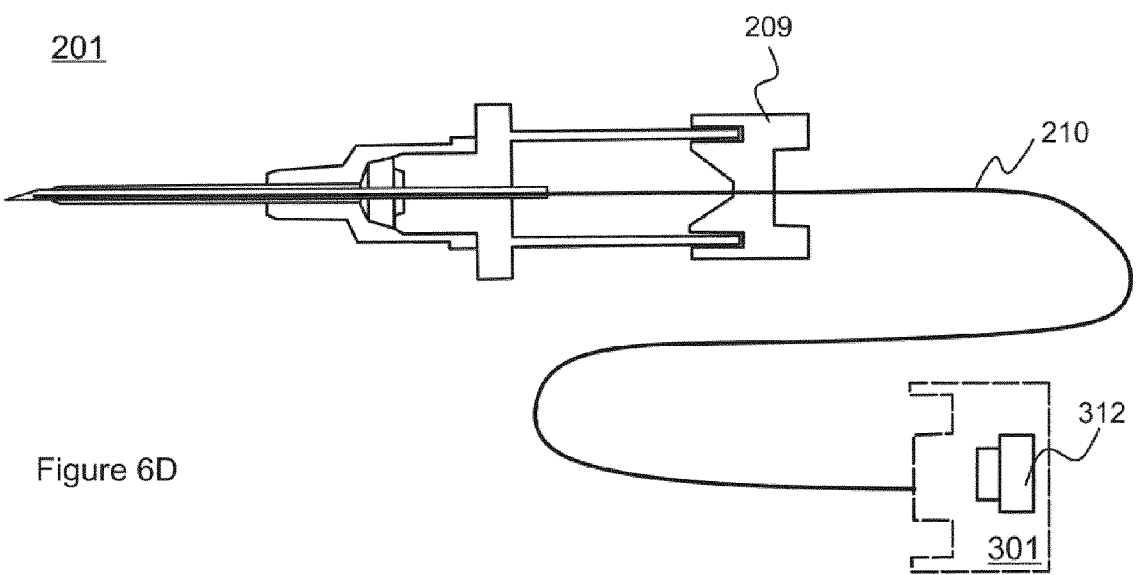

The catheter assembly shown in FIG. 6D is similar to that of FIGS. 6A and 6B, however, in this configuration the electronic module 301 is arranged at a distance from the adapter 209 that is connected to the disposable introducer needle 211. A distant connection in this case means that the only physical contact between the adapter 209 and the electronic module 301 is formed by the light guide 210.

The connection hub 206 of the introducer needle 211 of the catheter assembly 201 may be manufactured from a material that allows at least a portion of the light guide 210 to be visible to an outside observer. In particular this refers to a portion of the light guide 210 that is located between the adapter 209 (or more particularly its distal connection hub 209D) and the proximal end 205 of the needle member of the introducer needle 211. The connection hub of the introducer needle 206 is thus illuminated if the light source 312 is powered. The illumination is caused by light that is emitted through the walls of the light guide 210, and in particular its aforesaid portion. Said configuration is implemented to visualize at least one of the following illumination events at the connection hub 206 upon blood flow inside the lumen of the needle member 202 of the introducer needle 211 and further into the flashback chamber 207 of the introducer needle connection hub 206: illumination fading, change in illumination color and/or illumination fading along with change in illumination color.

The connection hub 206 within the distal section thereof may be preferably manufactured from a substantially semi-transparent material for preventing excessive skin illumination. In alternative configuration, the distal section of the introducer needle connection hub 206 comprises a layer of a non-transparent material for the same purpose.

Light emitted from the light source 312 may be focused by a lens 314 or another focusing device and is directed into the light guide 210, which transmits the light throughout the lumen 212 of the needle 202 and emits it at its distal end. Correspondingly, at the distal end 204 of the catheter needle 202 visible light of a predetermined wavelength appears. In accordance with the some embodiments, the light source 312 emits light of such wavelength that is strongly absorbed by blood, in particular by red blood cells, and/or by the walls of blood vessels (such as veins and arteries), but is relatively weakly absorbed by skin, fat and other surrounding tissues. In order to reach a blood vessel, catheter needle 202 has to penetrate tissues with different light scattering properties.

Figure 7A:
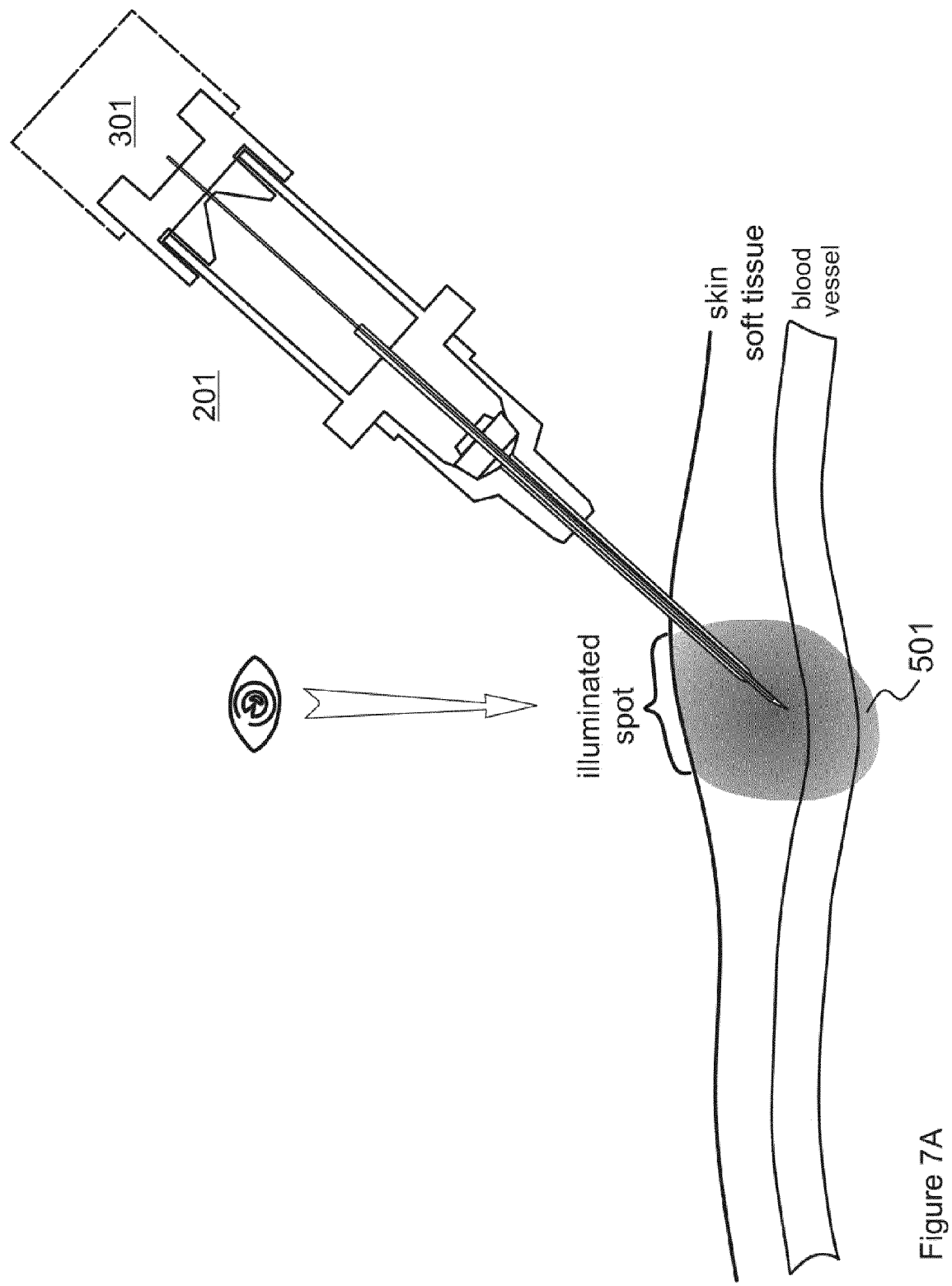
FIGS. 7A and 7B illustrate a process of blood vessel penetration by means of a catheter needle of an intravascular catheter assembly of the invention.
Figure 7B:
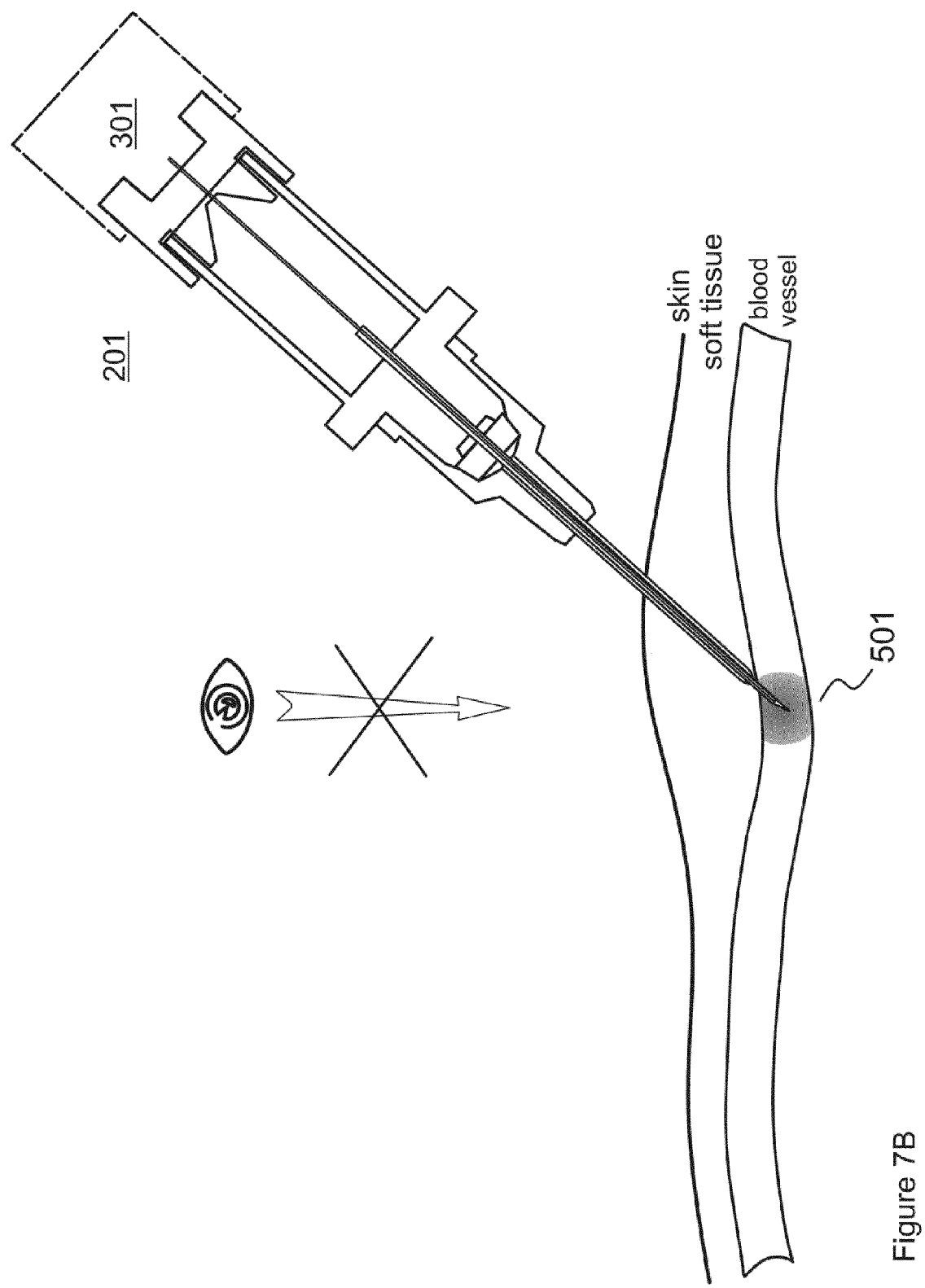

Referring now to FIG. 7A, when the tip of the needle of the catheter needle assembly 201 had already penetrated skin and tissues but has not yet entered a blood vessel, light 501 illuminates surrounding tissues and is partly reflected and scattered therefrom. Correspondingly, an illuminated spot (FIG. 7A) may be observed on the skin surface, and a clinician may follow the movement of the needle inside the skin to be aware of an exact position of the needle relative to a blood vessel. As soon as distal end of the introducer needle enters a blood vessel (FIG. 7B) in a way that blood entry aperture 204a and distal end of the light guide are immersed into blood, light is absorbed by blood and/or the walls of a blood vessel, and correspondingly the light spot 501 is not any more visible on the skin surface from outside. Since the penetration of a blood vessel wall by the distal end of the needle is a very rapid process, optical properties of surrounding the distal end of the needle tissues change momentarily from relatively low light absorption level to very high light absorption level. As can be seen from FIGS. 7A and 7B, light spot 501 becomes 'trapped' inside the blood vessel if the needle tip punctures the wall of a blood vessel and enters the lumen thereof. As a result, an outside observer (represented by eye pictogram) may easily visually detect the moment when light, otherwise visible on skin, disappears. This is indicative of a successful puncture of a vein or artery.

Above described phenomenon may be observed upon selecting light of a specific wavelength, such as green and yellow, for example. An event of absorption of light by blood upon successful introduction of the needle into a blood vessel may be registered by the eye and/or by any suitable detection system.

The aforesaid procedure is substantially adapted to perform a successful venipuncture in adults with relatively wide blood vessels having thick walls and a sufficient amount of blood flowing through them. However, some groups of patients may have small and thin blood vessels so that even upon successful entry of the needle tip inside the lumen of the vein, some light may still be visible on skin from the outside, thus causing confusion. The group of patients with thin and small vein comprises, in particular, children.

Referring now to FIGS. 8A and 8B, the catheter assembly with a light guide may be implemented to suit patients with both large and easily accessible blood vessels and patients with thin and small diameter blood vessels. The introducer needle of the catheter assembly may be provided with a light guide 210 terminating substantially at the opening on the distal end 204 (FIG. 8B). An arrangement of FIG. 8B suits particularly well for patients with large and easily accessible blood vessels, as disclosed above. Light guide 210 may also be configured to terminate substantially at some distance from the opening on the distal end 204 of the introducer needle (FIG. 8A). An arrangement of FIG. 8A suits particularly well for patients with small veins, such as children, as further disclosed.

FIGS. 8C and 8D illustrate light guide arrangements for small and large blood vessels respectively, but in configurations in which the light guide 210 is so wide to occupy substantially the whole volume of the needle lumen 212.

The shape of the light guide 210 at its distal end may vary depending on optical fibers availability, overall design and the like. An optical fiber, representing a light guide herein, may be simply cut (I) or have its end edges fritted (II), or be provided with a small lens positioned in the fiber tip so that fiber tip will acquire a spherical shape (III), as this is shown in FIGS. 8A-B.

Figure 9A:
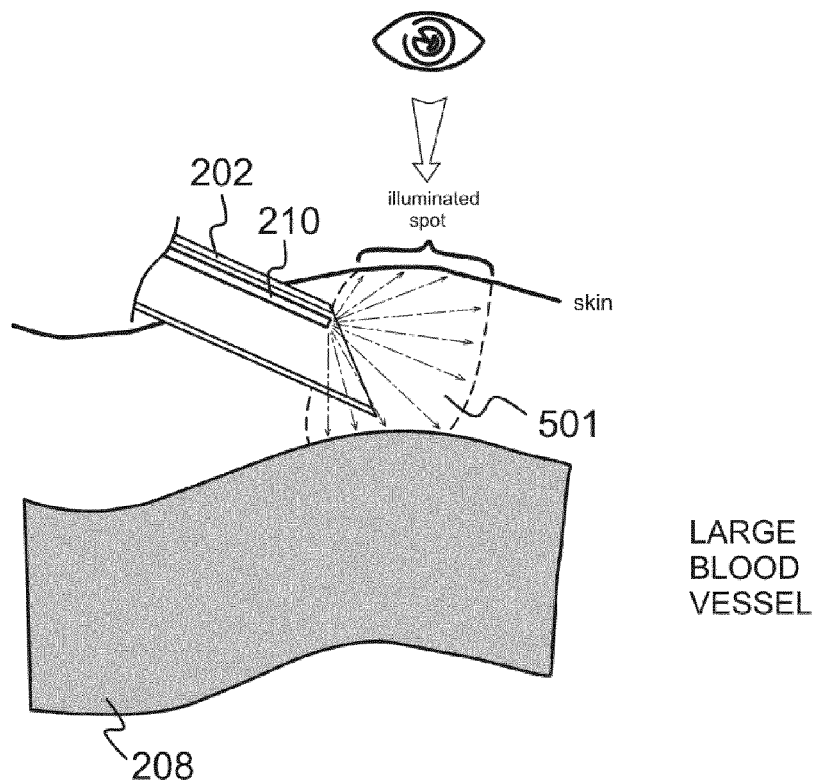
FIGS. 9A and 9B illustrate an intravascular catheter assembly operation on relatively large and easily accessible blood vessels.
Figure 9B:
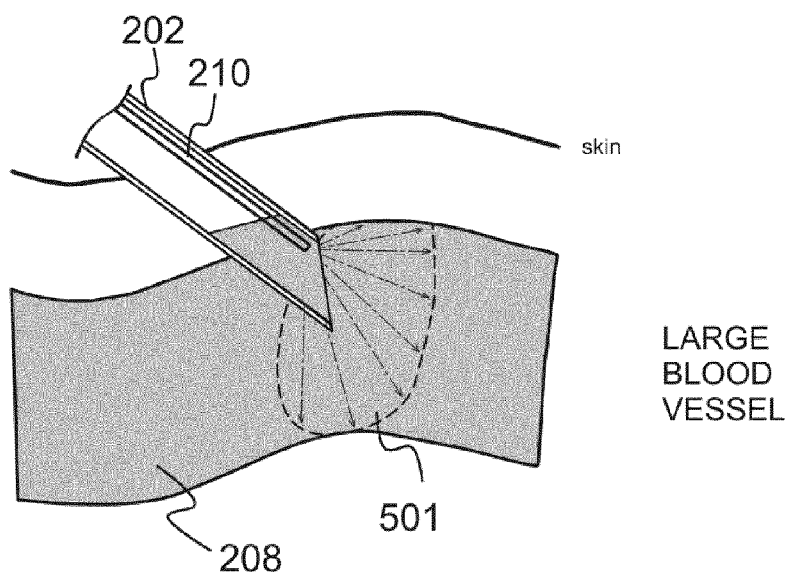

FIGS. 9A and 9B schematically illustrate an event of light absorption by blood happening, in particular, in large blood vessels. In accordance with a process shown in FIG. 7A, upon a successful penetration of a blood vessel by introducer needle distal end 204, light 501, otherwise visible on skin, rapidly disappears from view because of its absorption by blood and/or walls of blood vessels. The event of blood 208 flowing unobstructed into the lumen 212 of the needle member 202 of the introducer needle and thus blocking light 501 from sight of an outside observer is therefore illustrated by FIG. 9B.

Figure 10A:
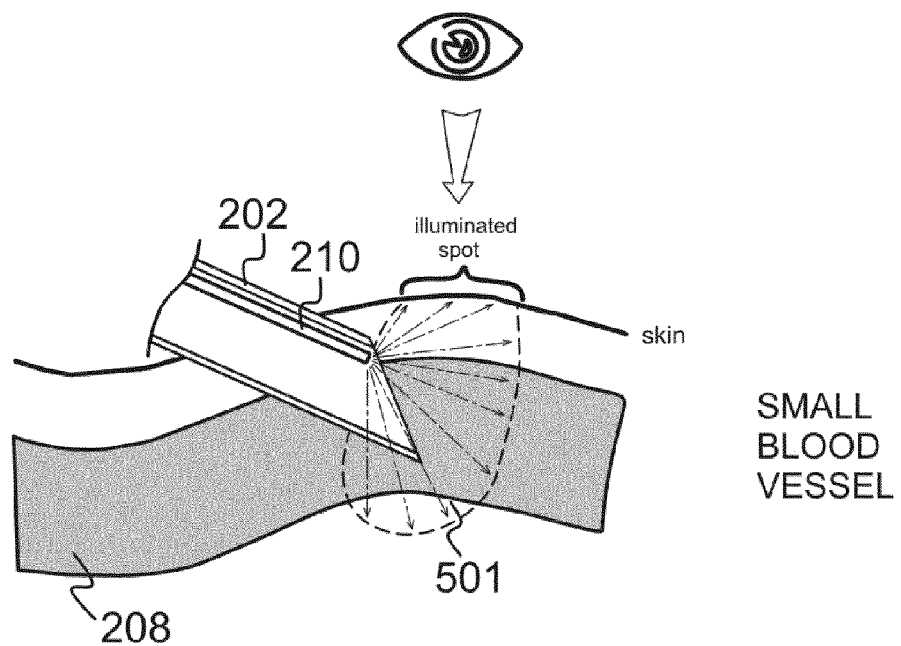
FIGS. 10A and 10B illustrate an intravascular catheter assembly operation on relatively thin and small blood vessels.
Figure 10B:
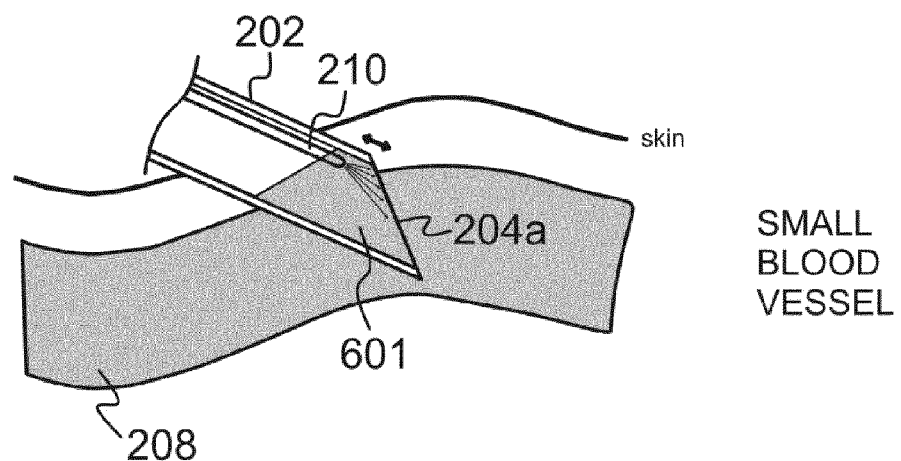

FIGS. 10A and 10B refer to catheter assembly configuration with a light guide 210 positioned to some extent away from the tip of the needle, in regards to patients with relatively small veins. Placing light guide 210 into close proximity to the blood entry aperture 204a, like illustrated by FIGS. 9A-B, may be a reliable option for patients with relatively large and easily accessible veins. However, when a blood vessel to be punctured has a relatively small diameter (cf. FIG. 10A: small vein, light guide is in close proximity to the needle tip), even in case of a successful penetration of the blood vessel some light 501 may possibly still 'leak', creating an illuminated spot to be observed on the skin and thus causing confusion. The reason for that is the close proximity of the light guide 210 to the needle opening. Therefore complete absorption of light cannot physically be accomplished for the reason that the vein may be too thin and small to accommodate the needle tip over its whole diameter. Then the light guide 210 remains at least partly outside the vein, and light may be at least partly scattered from the surrounding tissues and thus remain visible on the skin.

FIG. 10B shows a catheter assembly with a light guide 210 that is positioned at some distance (arrow) away from the blood entry aperture 204a. When the vein is successfully punctured with the introducer needle 211 with a light guide 210 arranged in the aforementioned way, blood would flow into the needle and fill up space indicated 601, thus blocking light 501 emitted from the tip of the light guide 210. Even a small amount of blood flowing inside the needle member 202 is sufficient to absorb light inside the needle member and, correspondingly, to completely block the light from the view of the observer. By an arrangement as shown in FIG. 10B a reliable method to confirm a successful event of blood vessel penetration in the case of small and thin blood vessels is provided.

This also applies equally to the light guide 210 shown in FIGS. 8C-D which is wide enough to occupy substantially the whole lumen of the needle member 202.

The distance between the blood entry aperture 204a and the distal end of the light guide 210 which is necessary for creating the space 601 shown in FIG. 10B, is mainly dependent on the maximum diameter of the lumen (i.e. inner diameter of the needle), but also on the diameter of the light guide, the wavelength and the optical power of the light passing through said light guide.

Figure 11:
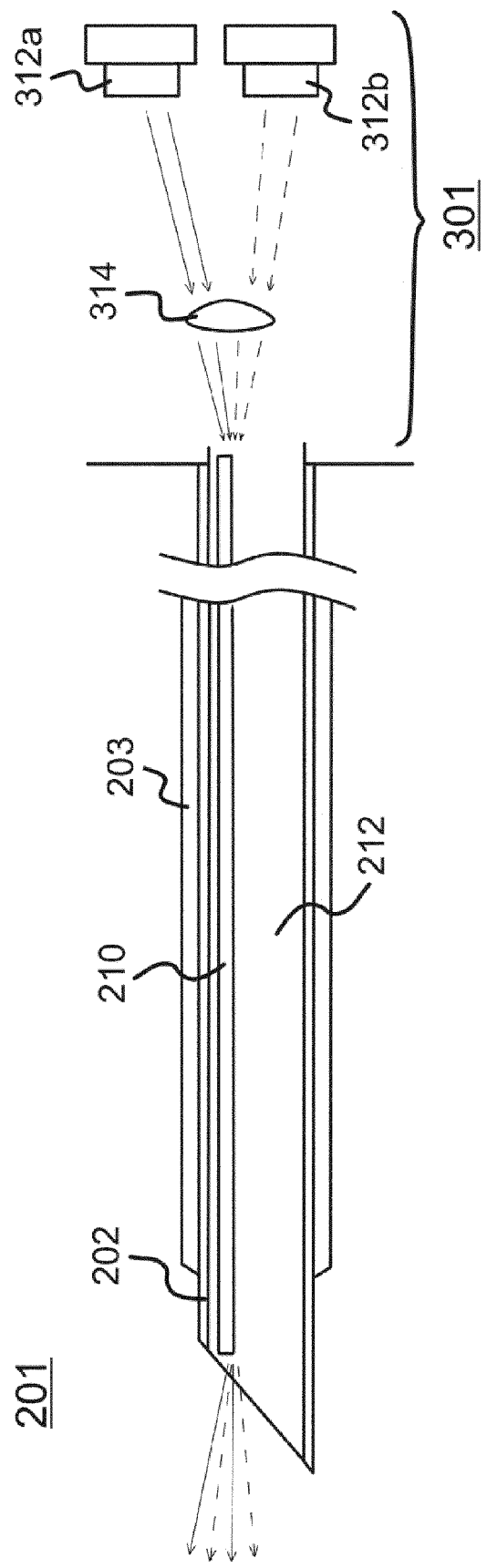
FIG. 11 schematically illustrates an intravascular catheter assembly connected to an electronic module device, comprising at least two light sources, in accordance to one embodiment.

In accordance with some embodiments, the catheter assembly is provided with more than one light source. Each light source is adjusted to emit light of certain wavelength, and all light sources may be adjusted to operate simultaneously. FIG. 11 schematically shows the catheter assembly 201 in accordance with an embodiment, in which the introducer needle 211 is mounted onto the electronic module 301 (the adapter is not shown) provided with two separate light sources 312a and 312b. Light sources may be realized e.g. as lasers, LEDs and other suitable light sources. Each light source is configured to emit light of a specific wavelength or wavelength range (cf. FIG. 11, solid and dashed arrows), and this light is further converged by lens 314 and directed into the light guide 210 that extends along the introducer needle. At least one light source is configured to emit light having a wavelength that is strongly absorbed by blood and the walls of blood vessels.

Figure 12:
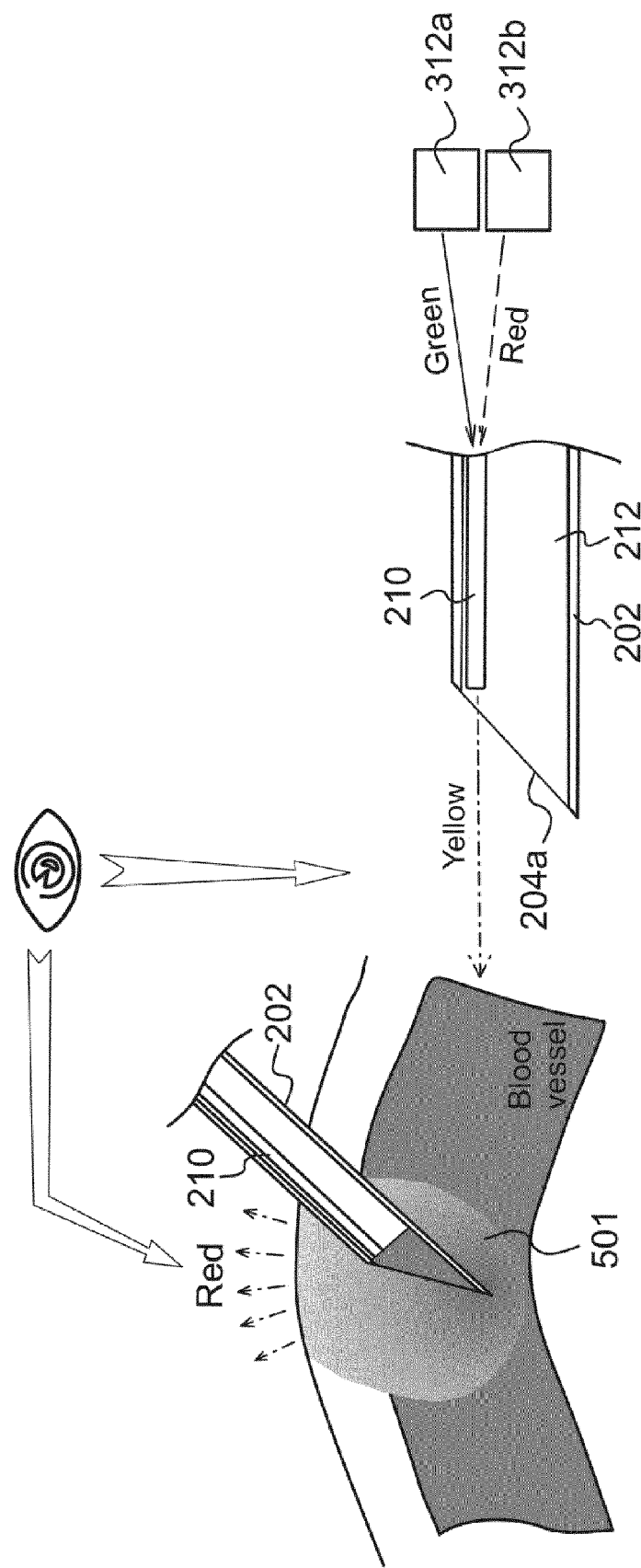
FIG. 12 illustrates an event of mixing light emitted by at least two light sources, and an event of blood vessel penetration by means of an introducer needle incorporating a light guide, which receives light emitted by said light sources.

A more detailed illustration of what has been explained above is given in FIG. 12. Light of two different colors, here green and red, is generated by two separate light sources 312a and 312b. The light sources may either operate simultaneously, or one light source may be temporary switched off. Control over the light sources may be implemented in the form of any suitable switch as mentioned previously, and/or by any other means that are technically compatible with the assembly, for example by a multi-positional slide switch and that enable turning on/off each light source individually when in far right/left or up/down positions, for example, and enabling turning on/off both light sources when in middle position. Light generated by light source(s) is further converged by lens, for example, and directed into the light guide 210.

By activating the light source(s) an outside observer thus would visually detect green, red or yellow light appearing at the distal end 204 of an introducer needle 202. Green or red light may be emitted by each light source separately, and yellow light is generated upon mixing green and red light, i.e. by activating both light sources at once. Since green light is particularly well absorbed by blood and the walls of blood vessels, it is preferred to utilize it for detecting the moment of penetration of the blood vessel wall by the needle tip.

Light of the other color, here red or yellow, may be utilized for visualization of a target blood vessel under the skin before penetration of said blood vessel. In case yellow light is utilized (as combination of green and red), greed light will be absorbed by blood upon entry of the needle tip into the lumen of blood vessel, and red light will still be visible. An outside observer may then detect a rapid change in color of the light, visible at the distal end of the needle, from yellow to red that is indicative of a successful puncturing of a blood vessel's wall and entering its lumen. Red light, herein, may be an important indicator of the exact position of a distal end of the needle inside blood vessel.

Figure 13A:
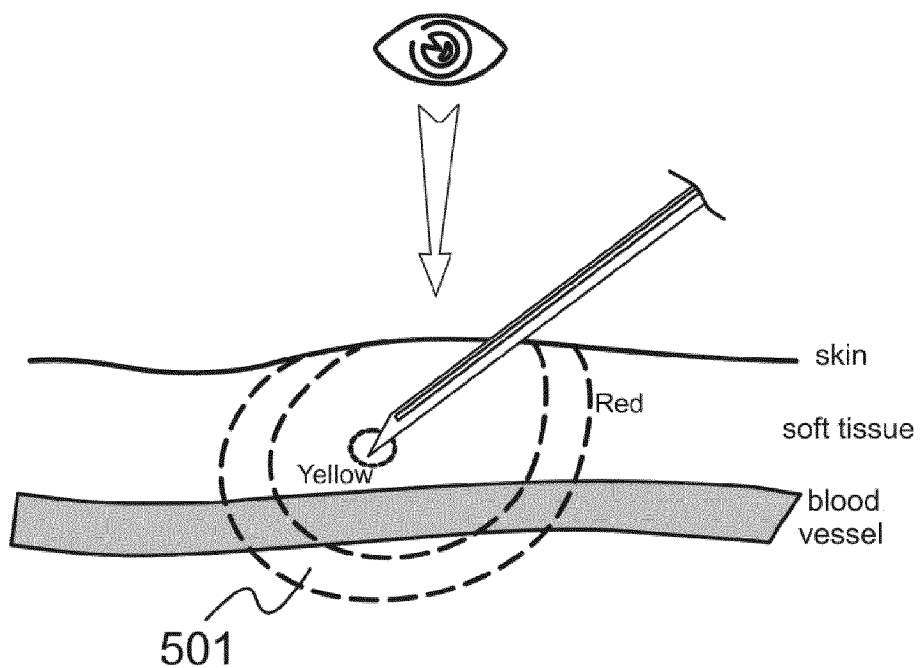
FIGS. 13A and 13B schematically represent a visually observable over the skin change in light color, which takes place upon penetrating the blood vessel by a catheter needle of an intravascular catheter assembly connected to an electronic module comprising at least two light sources.
Figure 13B:
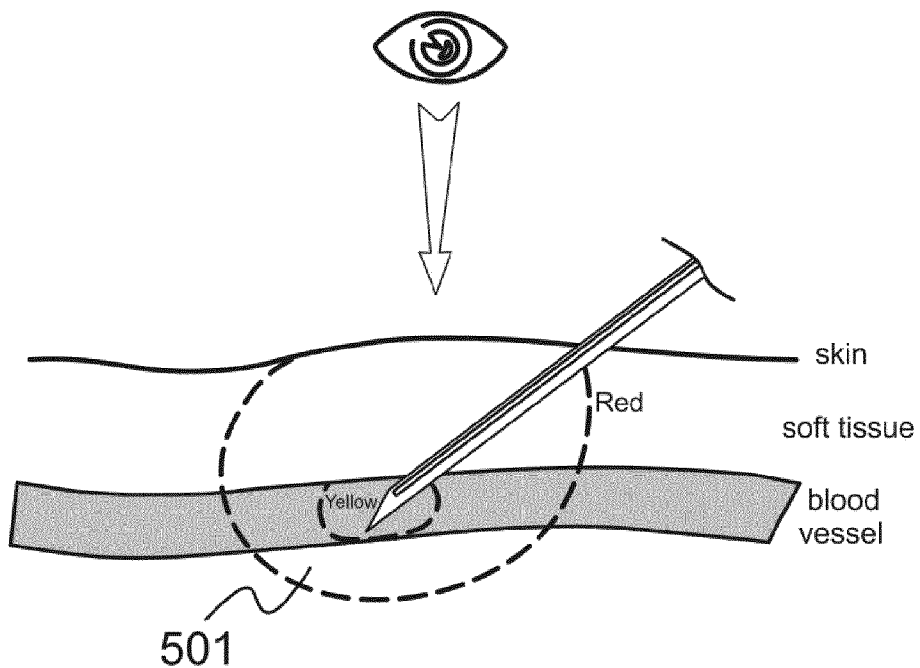

FIGS. 13A and 13B illustrate changes in light color, visually observable over the skin, while the distal end of an introducer needle penetrates blood vessel. Here yellow light is used as a combination of green and red light emitted from the light guide, and correspondingly, the needle's distal end. From an outside observer's point of view, shown by an eye pictogram, yellow light may be seen under the skin, while the introducer needle has already punctured the skin, but has not penetrated the blood vessel yet (FIG. 13A). Illuminated spot 501 has therefore a substantially yellow color. This color gradually turns red on the outer edges of the spot 501. The brightest yellow may thus be observed exactly where the tip of the catheter needle is, thus providing a tool of following the needle inside the skin. As soon as the needle enters the blood vessel (FIG. 13B) an outside observer may observe only red light.

Thus double detection means is provided, wherein light of at least two different wavelengths is utilized. Light of the first wavelength, here green, is provided in order to indicate the moment of penetration of the introducer needle into the lumen of the blood vessel. Light of the second wavelength, here red, is provided in order to visibly allocate a needle tip under the skin. In some cases, for example in case of blood vessels of big diameter or with thick walls, red light can also be trapped inside a blood vessel, so no light will be visible on skin surface.

It is to be understood, however, that abovementioned color examples are not intended to limit the purposes of the invention, and the light source(s) 312 of the electronic module 301 may be set up to generate light of any other suitable wavelength. For example, they may also produce white light. Absorption of the green light upon penetrating the vessel will then result in a color change to magenta.

The catheter assembly may be configured so that at least 40% of light that contributes to the total intensity of light emerging from the distal end of the light guide 210 is provided within a wavelength range corresponding to at least one absorption peak of blood hemoglobin, wherein hemoglobin absorption peaks are the following ranges: 375-455 nm, 393-373 nm, 502-582 nm, 515-595 nm and/or 536-616 nm.

The catheter assembly may in particular be configured so that at least 40% of light that contribute to the total intensity of light emerging from the distal end of the light guide is provided within a wavelength range between 500 and 580 nm.

The catheter assembly may also be configured so that at least 40% of light that contributes to the total intensity of light emerging from the distal end of the light guide is provided within a wavelength range between 600 and 800 nm.

If there are two light sources, a red light distribution pattern around the blood vessel may provide valuable information about the needle position outside and inside the blood vessel. For example, when the distal end of the needle 204 is located coaxially to the blood vessel, a butterfly-like pattern will appear on skin, while the blood vessel may appear as a dark line. It may be possible that the distribution of red light around the blood vessel, as disclosed above, may be highly asymmetric in case the tip 204b of an introducer needle hits a point opposite the puncture point on the wall of the blood vessel. This may lead to blood vessel damage during advancement of cannula tubing. Correct interpretation of red light distribution shapes around a blood vessel by skilled person may thus provide valuable information about the position of the needle inside the blood vessel and of the right moment for advancing the cannula. Moreover, if the skin area intended for puncturing is already bruised, red light may substantially simplify a procedure of needle advancement through bruised area.

Figure 14:
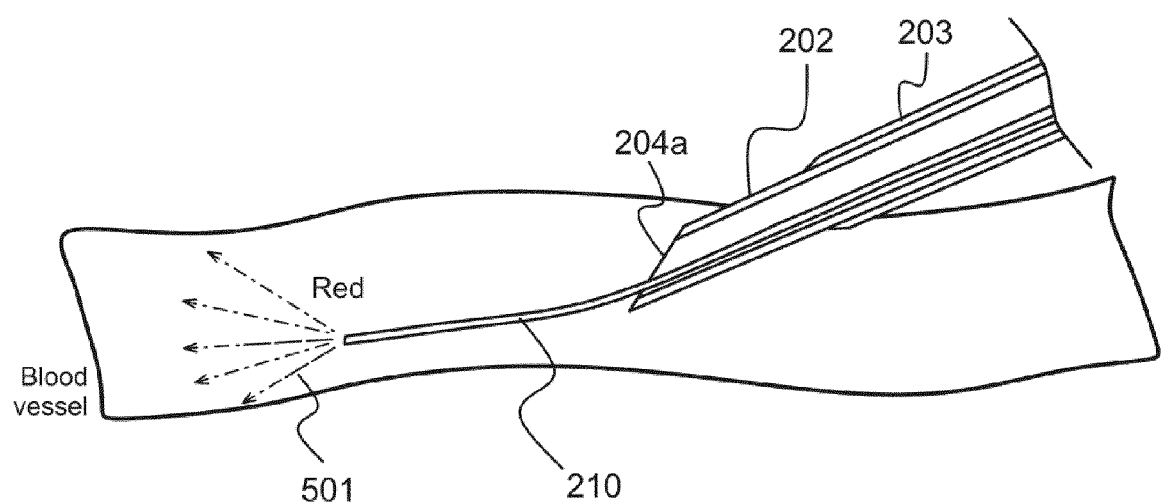
FIG. 14 illustrates an intravascular catheter assembly with a light guide extendable into a blood vessel.

In accordance with a further embodiment of the invention, which is illustrated in FIGS. 14 and 15, the catheter assembly is provided with an extendable light guide 210. FIG. 14 shows the distal end of an introducer needle 211 with a light guide 210 that protrudes from the distal end 204 of the needle member 202 into a blood vessel. The light guide 210 may be extended into a lumen of blood vessel to the distance of up to at least 1 cm. Red light 501 may become visible through skin at the distal end of a light guide. The fact that upon puncturing of blood vessel the light guide may be physically pushed into the blood vessel may be indicative of that the distal end of the needle member 202 is positioned correctly within the blood vessel's lumen. In addition, red light 501, moving forward upon protruding the light guide, may illuminate a blood vessel from inside.

Another advantage of an extendable light guide configuration is that the light guide may serve as a guide wire for advancement of the cannula tubing 203. When some part of a light guide 210, formed by an optical fiber, for example, is positioned inside the blood vessel, an advancement of the cannula tubing 203 into the blood vessel proceeds smoother, since the extended optical fiber also ensures the correct positioning of the cannula tubing inside the blood vessel even in case the introducer needle would accidentally slide from the blood vessel due to a force created by the movement of cannula tubing. The process of inserting a plastic cannula tubing 203 into blood vessel by means of the catheter assembly may be controlled with a high accuracy that substantially increases treatment efficiency. After the cannula tubing 203 is positioned inside the blood vessel, the introducer needle with the light guide 210 may be safely removed from the blood vessel. Such a feature might be especially useful for placement of arterial catheters and central venous catheters.

Figure 15A:
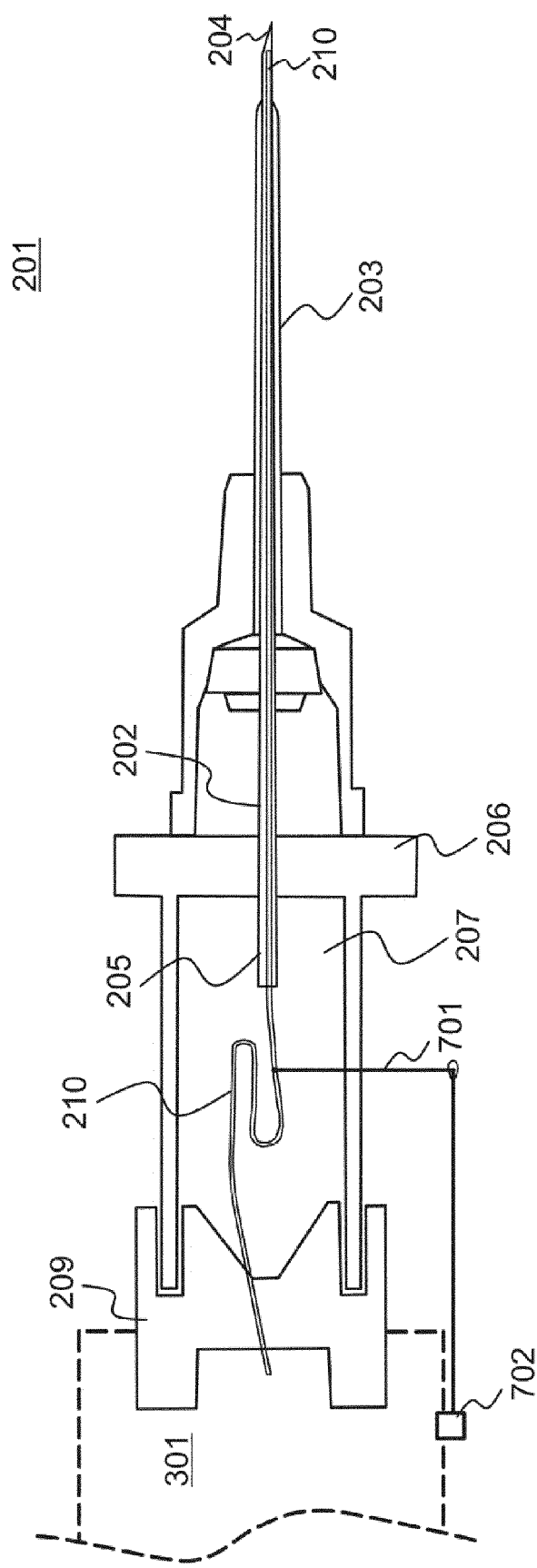
FIGS. 15A and 15B illustrate an intravascular catheter assembly with an extendable light guide in more detail.
Figure 15B:
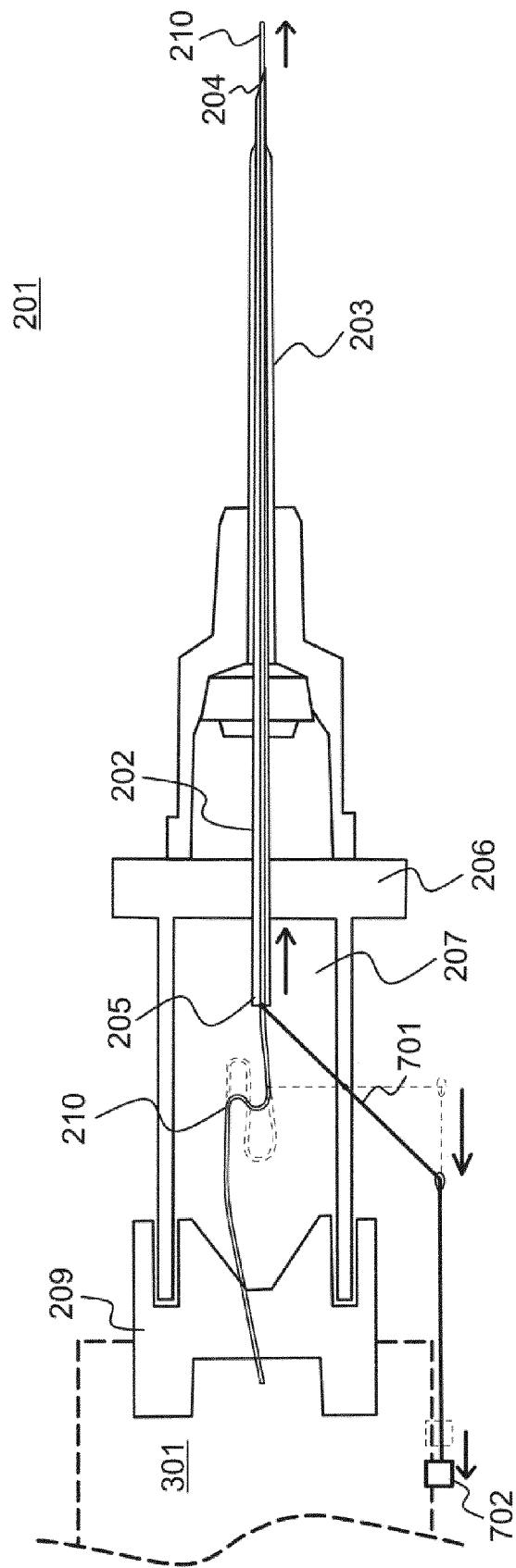

FIG. 15A illustrates an arrangement of an extendable light guide 210 within the introducer needle 211 and the flashback chamber 207 formed inside the connection hub 206. A disposable ready-packed catheter assembly 201 is provided with an extendable light guide 210, partly folded inside the flashback chamber 207. The light guide 210 is thus arranged into a fold, such as a loop, a zigzag turn, a spiral or the like. The distal end of the light guide 210 does not project over the distal end 204 of the introducer needle. The light guide 210 may be rolled, folded or otherwise gathered inside a flashback chamber 207 in any technically implementable way. The light guide 210 is kept in a folded state by means of a pushing mechanism 701 that is operated by a releasing switch 702. The releasing switch 702 may be arranged on the outer surface of the electronic module 301 (FIG. 15A), or on the outer surface of the adapter 209, whatever is technically beneficial. The releasing switch 702 may be configured as a pushbutton switch, a lever switch, a slide switch with a seesaw action and the like. A releasing action of the releasing switch 702 may be adapted to be automatic or to be triggered manually. In the latter case, by manual sliding the releasing switch 702 forward/backward, a clinician may release the folded light guide 210 from connector wires of pushing mechanism 701 and make the light guide 210 to extend forward, out of the opening at the distal end 204 of the needle member 202 as it is illustrated in FIG. 15B. The pushing mechanism 701 may comprise connector wires, springs and the like to be configured on the basis of any technically suitable means. The releasing switch 702 may be realized in any technically implementable way. The light guide 210 in its released state is adapted to serve as a guide wire for pushing a cannula into the blood vessel.

The light guide may be kept in a folded state also within the adapter 209, for example in a separate chamber provided therein.

Figure 16:
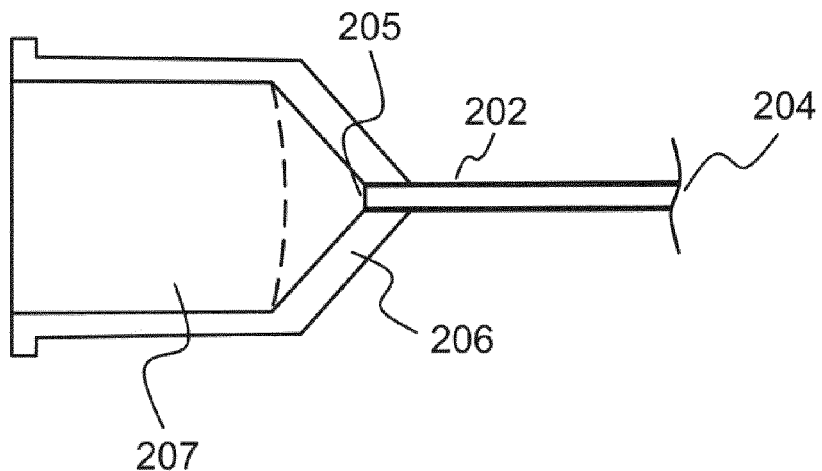
FIG. 16 illustrates a funnel-like connection hub of the introducer needle in accordance with some embodiment.

In accordance with another embodiment, the catheter assembly comprises an introducer needle 211 provided with a connection hub 206 configured in the form of a funnel (FIG. 16). Here the proximal end 205 of the needle member 202 of the introducer needle is integrated within the vertex of the funnel cone and terminates therein. This is in contrast to prior art solutions in which the proximal end 205 of the needle member 202 projects into the flashback chamber 207 of the connection hub 206 (cf. FIG. 1B). A funnel-like configuration provides a sloped surface for the distal end of a flashback chamber 207 and thus allows a smooth, fast and accurate slide-like insertion of the light guide 210 into the needle member 202 via the connection hub 206.

Figure 17:
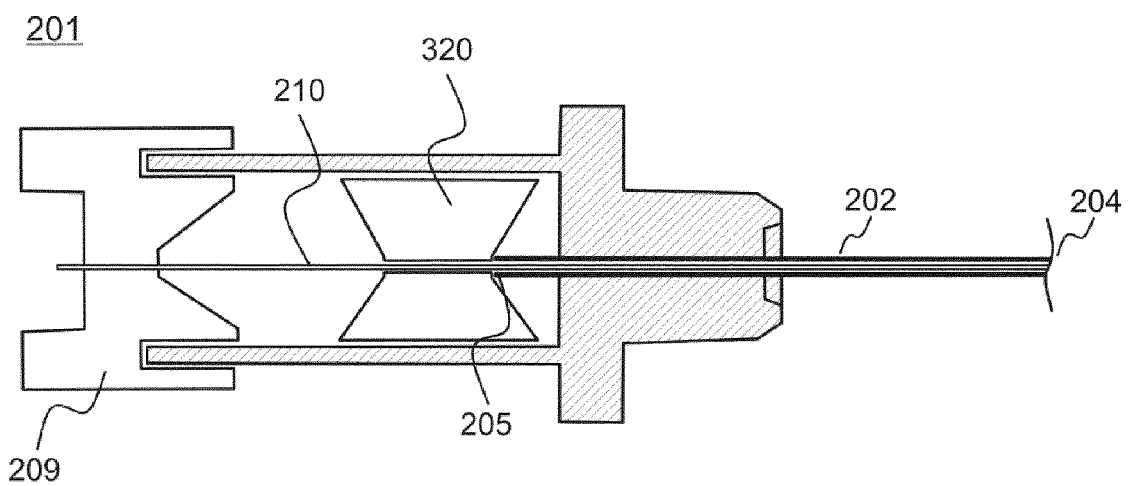
FIG. 17 illustrates an intravascular catheter assembly, wherein introducer needle comprises a two-sided funnel-like insert inside a connection hub flashback chamber, in accordance with some embodiment.

In another embodiment the catheter assembly comprises an introducer needle provided with a connection hub 206 that comprises, in turn, a separate member 320 within the flashback chamber 207 thereof (cf. FIG. 17). Said member 320 is preferably configured as a double sided funnel provided with two funnel bases pointing to opposite directions and two funnel apexes pointing towards each other, and comprising a bore which pierces said member 320 throughout. The member 320 further comprises apertures on both recesses of the double sided funnel, respectively, wherein an inner diameter of the bore is adapted to allow free sliding of the light guide 210 therethrough. The apertures on both recesses of the double sided funnel are adjusted to be coaxial to the proximal end 205 of the needle member 202, thus ensuring a smooth insertion of the light guide 210 into the needle member 202 via the connection hub 206.

In another aspect of the invention, a method for intracutaneous localization of the blood vessels, for the detection an exact moment of intravascular penetration and for safeguarding the blood vessel from being damaged from inside is provided in accordance with aforesaid embodiments, said method comprising at least several of the following steps:

a. locating a blood vessel, suitable to perform vascular access procedure;
b. obtaining the intravascular catheter assembly 201 provided with the electronic module 301;
c. activating the light source(s) 312 of the electronic module 301 for light to be observed on the distal end 204 of the needle member 202 of the introducer needle 211;
d. puncturing the skin with the introducer needle 211 of the intravascular catheter assembly 201;
e. localizing a blood vessel position intracutaneously by monitoring illumination events at the distal end 204 of the needle member 202 of the introducer needle 211;
f. detecting the moment when the distal end 204 of the needle member 202 of the introducer needle 211 penetrates the wall of a blood vessel and enters the lumen of a blood vessel by observing at least one of the following illumination events at the introducer needle distal end 204: instant disappearance of illumination, rapid illumination fading, rapid change in light color and/or rapid illumination fading along with rapid change in light color, wherein said events are dependent on the light wavelength utilized;
g. ensuring a correct position of the introducer needle 211 inside a blood vessel lumen by monitoring illumination events at the introducer needle distal end 204;
h. advancing a cannula tubing 203 inside a lumen of blood vessel;

In accordance with aforesaid aspect of the invention, said method may be applied equally efficiently to patients of any age group, independent of size, diameter and depth of blood vessels thereof. Individual steps said method comprises are above disclosed in this document in more detail and are not to be repeated.

In still another aspect of the invention, a fast and accurate method for placing an intravascular catheter into a blood vessel is provided in accordance with aforesaid embodiments, wherein an efficiency of said method is independent of size, location depth and condition of blood vessels, and wherein said method comprises at least several of the following steps:

a. locating a blood vessel, suitable to perform vascular access procedure;
b. visual or performed by palpation condition determination of a blood vessel to be punctured;
c. obtaining the intravascular catheter assembly 201 provided with the electronic module 301;
d. activating the light source(s) 312 of the electronic module 301 for light to be observed on the distal end 204 of the needle member 202 of the introducer needle 211;
e. puncturing the skin with the introducer needle 211 of the intravascular catheter assembly 201;
f. localizing a blood vessel position intracutaneously by monitoring illumination events at the distal end 204 of the needle member 202 of the introducer needle 211;
g. detecting the moment when the distal end 204 of the needle member 202 of the introducer needle 211 penetrates the wall of a blood vessel and enters the lumen of a blood vessel by observing at least one of the following illumination events at the introducer needle distal end 204: instant disappearance of illumination, rapid illumination fading, rapid change in light color and/or rapid illumination fading along with rapid change in light color, wherein said events are dependent on the light wavelength utilized;
h. ensuring a correct position of the introducer needle 211 inside a blood vessel lumen by monitoring illumination events at the introducer needle distal end 204;
i. extending a cannula tubing 203 inside a blood vessel lumen;
j. withdrawing the introducer needle 211 from a blood vessel, while the cannula tubing 203 is set inside a blood vessel;
k. securing the cannula tubing 203 over the skin of a patient and connecting an appropriate system thereto.

Important aspects of the invention are summarized in the following sentences:

1. A peripheral intravascular assembly for catheterization (201) comprising:
   a. an introducer needle (211) comprising a connection hub (206) and a needle member (202), wherein the needle member (202) has a lumen (212), a distal end (204) provided with an opening (204a) and a proximal end (205),
   b. a light guide (210) having a distal end and a proximal end and extending along the lumen of the needle member (202),
   c. an adapter (209) to which the light guide (210) is fixed or mounted,
   wherein the adapter (209) is provided with an interface for a light source,
   wherein the adapter (209) is connected to the connection hub (206) of the introducer needle (211),
   wherein the adapter (209) is adapted to form a leak-proof barrier between blood and an interface for a light source.

2. The assembly of sentence 1, wherein the lumen (212) of the needle member (202) has a maximum diameter d, and wherein the distal end of the light guide (210) is arranged inside the lumen (212) of the needle member (202), but spaced apart from the opening (204a) at the distal end (204) of the needle member (202) by a distance that is greater than 0.1 mm and smaller than 20 mm.

3. The assembly of any of the sentences 1 or 2, comprising a pushing mechanism (701) that is configured to move the light guide (210), upon actuation of the pushing mechanism by a user, along the lumen (212) of the needle member (202) between a projecting position, in which the distal end of the light guide (210) projects over the distal end (204) of the needle member (202) at least by a distance 2d, and a retracted position, in which the distal end of the light guide (210) is spaced apart from the opening (204a) at the distal end (204) of the needle member (202) at least by a distance 0.1 mm, wherein d is the maximum diameter of the lumen (212) of the needle member (202).

4. The assembly of any of the preceding sentences, wherein the light guide (210) is fixed or mounted at a close vicinity to the adapter (209).

5. The assembly of any of the preceding sentences further comprising a cannula tubing (203) surrounding at least a portion of the needle member (202).

6. The assembly of any of the preceding sentences further comprising at least one light source (312; 312a).

7. The assembly of any of sentences 1 to 5, comprising two separate light sources (312a; 312b) that are configured to be operated simultaneously and/or subsequently.

8. The assembly of any of the preceding sentences further comprising an electronic module (301) that is configured to power the light source (312; 312a).

9. The assembly of any of the preceding sentences, wherein the light source (312; 312a) is arranged within the electronic module (301).

10. The assembly of any of the sentences 1 to 6, wherein the light source (312; 312a) is fixed on mounted at the adapter (209).

11. The assembly of any of the sentences 1 to 6, wherein the light source (312; 312a) is fixed on mounted at the proximal end of the light guide (210).

12. The assembly of sentence 6, wherein the adapter (209) is connectable or connected to the light source (312, 312a) so, that light emitted by the light source (312, 312a) is capable of entering the light guide (210) or transmitted into the light guide preferably at its proximal end, but blood flowing through the lumen (212) of the needle member (202) is prevented from contacting the light source (312, 312a).

13. The assembly of any of the sentences 1 to 9, wherein the adapter (209) is integrally formed as one functional unit with the electronic module (301).

14. The assembly of any of the sentences 1 to 13, wherein the adapter (209) is integrally formed as one functional unit with the introducer needle (211).

15. The assembly of any of the sentences 1 to 13, wherein the adapter (209) forms an integral functional unit with the electronic module (301) and the introducer needle (211).

16. The assembly of any of the sentences 1 to 13, wherein the adapter (209) is integrally formed as one functional unit with the needle member (202).

17. The assembly of any of the sentences 1 to 15, wherein the adapter (209) is arranged at a distance from the proximal end of the needle member (202).

18. The assembly of any of the preceding sentences, comprising safety means for preventing a user of being wounded by the distal end (204) of the needle member (202), wherein said safety means are configured as an automatic retraction-extension mechanism for the light guide (210) comprising the adapter being configured as a two-unit member, which comprises an outer unit (219), which has a central aperture (219a), and a central unit (229), which is positioned within the central aperture (219a) of the outer unit, wherein the central unit (229) is configured to be movable within the aperture (219a) of the outer unit and is provided with a bore (229a) to receive the light guide (210), said bore (229a) being sealed liquid-tightly against the light guide (210), wherein an operation of the automatic retraction-extension mechanism is based on automatic rotational and/or translational movement of the central unit (229) within the aperture (219a) of the outer unit (219) upon mounting or dismounting the introducer needle (211) onto the electronic module (301) or from the electronic module (301), respectively.

19. The assembly of any of the preceding sentences, wherein an outer diameter of the adapter (209) is larger than an outer diameter of the connection hub (206) of the introducer needle (211).

20. The assembly of any of the sentences 1 to 9 and 12 to 19, wherein the connection hub (206) is provided with an inner chamber, in particular, a flashback chamber and wherein the proximal end (205) of the needle member (202) is arranged at or within the inner chamber of the connection hub so, that blood flowing from the distal end (204) through the lumen (212) of the needle member (202) will exit the proximal end (205) of the needle member and enter or be received by the inner chamber of the connection hub (206) and wherein the adapter (209) provides a sealing for the light source from blood in the inner chamber.

21. The assembly of sentence 20, wherein the connection hub is provided with a flashback chamber (207) as the inner chamber for receiving blood exiting from the proximal end of the needle member.

22. The assembly of sentence 21, wherein the flashback chamber (207) has a body portion shaped as a funnel, wherein the proximal end (205) of the needle member (202) of the introducer needle (211) is integrated within the vertex of the funnel and terminates therein so as to allow a fast and accurate insertion of the light guide (210) into the needle member (202) via connection hub (206).

23. The assembly of sentences 20 or 21, comprising a separate member (320) positioned inside the connection hub (206), said separate member (320) being configured as a double sided funnel having two funnel bases pointing to opposite directions, wherein the funnel comprises a central through-bore ending at apertures on both funnel bases, wherein an inner diameter of the bore is adapted to allow free sliding of the light guide (210) therethrough, and wherein the apertures on both bases of the funnel are coaxial to the proximal end (205) of the needle member (202) so as to allow a smooth insertion of the light guide (210) into the needle member (202) via the connection hub (206).

24. The assembly of any of the preceding sentences, wherein a connection between the adapter (209) and the connection hub (206) of the introducer needle (211) and/or the electronic module (301) is liquid-tight, in particular blood-tight.

25. The assembly of any of the preceding sentences, wherein the light guide (210) is an optical fiber.

26. The assembly of any of the preceding sentences, wherein the light guide (210) is received in the lumen (212) of the needle member (202) such that the light guide is capable of sliding along the lumen if a tensile force is applied to one end of the light guide.

27. The assembly of any of the preceding sentences, wherein the light guide (210) is arranged to extend through the adapter (209).

28. The assembly of any of the sentences 20 and 21, wherein the inner chamber of the connection hub (206) and/or the proximal end (205) of the needle member (202) is/are arranged at a distal side of the adapter (209D) and the proximal end of the light guide (210) is arranged at the proximal side of the adapter (209P) opposite to the distal side (209D).

29. The assembly of any of the sentences 20, 21 and 28, wherein the adapter (209) is arranged in between the inner chamber of the connection hub (206) and the light source (312, 312a) thus separating thereof.

30. The assembly of sentences 1 and 8, wherein the adapter (209) comprises at least two adapter parts being connected or connectable to each other and wherein the first adapter part is connected or connectable with the connection hub (206) and the second adapter part is connected or connectable with the electronic module (301).

31. The assembly of sentence 1, further comprising a sealing around the light guide (210) within the lumen (212) of the needle member (202) substantially at the proximal end (205) of the needle member (202) or outside the lumen (212) of the needle member (202) at the proximal end (202) thereof.

32. The assembly of any of the preceding sentences, wherein the introducer needle (211) is tubular.

33. A method for assembling a peripheral intravascular assembly for catheterization, said method comprises:
   a. providing the adapter (209) and the light guide (210);
   b. pre-mounting or fixing the light guide (210) to the adapter (209) so, that a distal end and a following proximally extending towards the adapter section of the light guide are accessible;
   c. providing the introducer needle (211);
   d. inserting the distal end and the following proximally extending towards the adapter section of the light guide (210) from the proximal end (205) of the needle member (202) into its lumen (212) so, that the light guide (210) extends through the lumen (212);
   e. leak-proof connecting the adapter (209) to the connection hub (206) of the introducer needle (211).

34. A peripheral intravascular assembly of any of the preceding sentences for use in an intracutaneous localization of blood vessels and/or for detection the moment of an intravascular penetration and/or for safeguarding the blood vessel from being damaged from inside is provided.

35. A peripheral intravascular assembly for catheterization (201) comprising:
   a. a tubular introducer needle (211) comprising a connection hub (206) and a needle member (202), wherein the needle member (202) has a lumen (212), a distal end (204) and a proximal end (205),
   b. a cannula tubing (203) surrounding at least a portion of the needle member (202),
   c. at least one light source (312; 312a),
   d. an electronic module (301) that is configured to power the light source,
   e. a light guide (210) having a distal end and a proximal end and extending along the lumen of the needle member (202),
   f. an adapter (209) to which the proximal end of the light guide (210) is fixed, wherein the adapter is releasably connected to the electronic module (301) and fixedly or releasably connected to the connection hub of the introducer needle so that light emitted by the light source (312; 312a) is capable of entering the light guide (210), but blood flowing through the lumen (212) of the needle member (202) is prevented from contacting the light source (312; 312a).

36. The assembly of sentence 35, wherein at least 40% of light that contributes to the total light intensity emerging from the distal end of the light guide (210) has a wavelength between 500 nm and 580 nm.

37. The assembly of any of the sentences 35 or 36, wherein at least 40% of light that contributes to the total light intensity emerging from the distal end of the light guide (210) has a wavelength between 600 nm and 800 nm.

38. The assembly of any of the sentences 35 to 37, wherein at least 75% of light that contributes to the total light intensity emerging from the distal end of the light guide (210) has a wavelength between 500 nm and 800 nm.

39. The assembly of any of the sentences 35 to 37, wherein the light source (312; 312a) is capable of producing white light.

40. The assembly of any of the preceding sentences, wherein the lumen (212) of the needle member (202) has a maximum diameter d, and wherein the distal end of the light guide (210) is fixedly arranged inside the lumen (212) of the needle member (202), but spaced apart from the distal end (204) of the needle member (202) by a distance that is greater than d/5 and smaller than 5d.

41. The assembly of sentence 40, wherein the distance is greater than d/2 and smaller than 2d.

42. The catheter assembly of any of the sentences 8 and 35 to 39, comprising a pushing mechanism (701) that is configured to move the light guide (210), upon actuation of the pushing mechanism by a user, along the lumen (212) of the needle member (202) between a projecting position, in which the distal end of the light guide (210) projects over the distal end (204) of the needle member (202) at least by a distance 2d, and a refracted position, in which the distal end of the light guide (210) is spaced apart from the distal end (204) of the needle member (202) at least by a distance d/2, wherein d is the maximum diameter of the lumen (212) of the needle member (202).

43. The assembly of sentence 42, wherein, in the retracted position, a part of the light guide is arranged in a folded configuration within a flashback chamber (207), which is provided in the connection hub (206), or an inner chamber provided in the adapter, and wherein, in the projecting position, the light guide is unfolded so that it projects over the distal end of the needle member (202).

44. The assembly of sentence 43, wherein the pushing mechanism (701) is operable by a switch (702).

45. The assembly of any of the sentences 35 to 43, wherein the adapter (209) is integrally formed as one piece with the electronic module (301).

46. The assembly of any of the sentences 35 to 44, comprising safety means for preventing a user of being wounded by the distal end (204) of the needle member (202), wherein said safety means are configured as an automatic retraction-extension mechanism for the light guide (210) comprising the adapter being configured as a two-unit member, which comprises an outer unit (219), which has a central aperture (219a), and a central unit (229), which is positioned within the central aperture (219a) of the outer unit, wherein the central unit (229) is configured to be movable within the aperture (219a) of the outer unit and is provided with a bore (229a) to receive the light guide (210), said bore (229a) being sealed liquid-tightly against the light guide (210), wherein an operation of the automatic retraction-extension mechanism is based on automatic rotational and/or translational movement of the central unit (229) within the aperture (219a) of the outer unit (219) upon mounting or dismounting the introducer needle (211) onto the electronic module (301) or from the electronic module (301), respectively.

47. The assembly of sentence 46, wherein
   a. at an initial position, when the introducer needle (211) is dismounted from the electronic module (301), the central unit (229) is located at a most distal position within the aperture (219a) of the outer unit (219a) so that the light guide (210), which extends slideably along the lumen of the needle member, projects out of the distal end (204) of the needle member (202);
   b. the central unit (229) is configured to rotationally and/or translationally shift backward within the aperture (219a) of the outer unit (219) upon connection of the electronic module (301) to the adapter (209), which action causes the light guide (210) to retract inside the lumen of the needle member (202), thus allowing the user to perform catheterization;

c. the central unit (229) is configured to rotationally and/or translationally shift forward within the aperture (219*a*) of the outer unit (219*a*) upon disconnection of the electronic module (301) from the adapter (209), which action causes the light guide (210) again to extend out of the lumen of the needle member (202).

48. The assembly of any of the sentences 35 to 47, wherein the adapter (209) is manufactured from a material that is semi-transparent for visible light.

49. The assembly of any of the sentences 35 to 48, wherein the connection hub (206) of the introducer needle is manufactured from a material that allows at least a portion of the light guide (210) to be visible to an outside observer.

50. The assembly of sentence 49, wherein the portion is located between the adapter (209D) and a proximal end (205) of the needle member (202).

51. The assembly of sentence 50, wherein the connection hub (206) of the introducer needle (211) is illuminated when the light source (312) is powered, said illumination being caused by light that is emitted by a lateral surface area of the light guide (210).

52. The assembly of any of the sentences 50 or 51, wherein the connection hub (206) is provided with a flashback chamber (207), and wherein the assembly is configured to visualize at least one of the following illumination events at the connection hub (206) of the introducer needle (211) upon blood flow inside the lumen of the needle member (202) and further on into the flashback chamber (207) of the introducer needle connection hub (206), said illumination events comprising illumination fading, change in illumination color, illumination fading along with change in illumination color.

53. The assembly of any of the sentences 35 to 52, wherein the adapter (209) has a textured outer surface.

54. The assembly of any of the sentences 35 to 53, wherein an outer diameter of the adapter (209) is larger than an outer diameter of the connection hub (206) of the introducer needle (211).

55. The assembly of any of the sentences 35 to 54, wherein a distal portion of the connection hub (206) is manufactured from a material which is semi-transparent or opaque for visible light.

56. The assembly of any of the sentences 35 to 55, wherein the connection hub (206) is provided with a flashback chamber (207) having a body portion that is shaped as a funnel, wherein the proximal end (205) of the needle member (202) of the introducer needle (211) is integrated within the vertex of the funnel and terminates therein so as to allow a fast and accurate insertion of the light guide (210) into the needle member (202) via connection hub (206).

57. The assembly of any of the sentences 35 to 55, wherein the connection hub (206) is provided with a flashback chamber (207), and wherein the assembly comprises a separate member (320) positioned inside the connection hub (206), said separate member (320) being configured as a double sided funnel having two funnel bases pointing to opposite directions, wherein the funnel comprises a central through-bore ending at apertures on both funnel bases, wherein an inner diameter of the bore is adapted to allow free sliding of the light guide (210) therethrough, and wherein the apertures on both bases of the funnel are coaxial to the proximal end (205) of the needle member (202) so as to allow a smooth insertion of the light guide (210) into the needle member (202) via the connection hub (206).

58. The assembly of any of the preceding sentences 35 to 57, wherein a connection between the adapter (209) and the connection hub (206) of the introducer needle (211) and/or the electronic module (301) is liquid-tight.

59. The assembly of any of the preceding sentences 35 to 58, wherein the connection hub (206) is provided with a flashback chamber (207), and wherein the proximal end (205) of the needle member (202) is arranged in the flashback chamber (207).

60. The assembly of any of the preceding sentences 35 to 59, wherein the light guide (210) is an optical fiber.

61. The assembly of any of the preceding sentences 35 to 60, wherein the light guide (210) is received in the lumen (212) of the needle member (202) such that the light guide (210) is capable of sliding along the lumen if a tensile force is applied to one end of the light guide.

62. A peripheral intravascular assembly for catheterization (201) comprising:
   a. a tubular introducer needle (211) comprising a connection hub (206) and a needle member (202) having a lumen (212), a distal end (204) and a proximal end (205),
   b. a cannula tubing (203) surrounding at least a portion of the needle member (202),
   c. an electronic module (301) comprising a light source (312; 312*a*),
   d. a light guide (210) having a distal end and a proximal end and extending along the lumen of the needle member (202), wherein
      i) the proximal end of the light guide (210) is optically coupled to the light source such that light emitted by the light source (312) is capable of entering the light guide (210), and wherein
      ii) the distal end of the light guide (210) is arranged inside the lumen of the needle member (202), but spaced apart from the distal end of the needle member (202), by a distance that is greater than d/5 and smaller than 5d.

63. The catheter assembly of sentence 62 wherein the distance is greater than d/2 and smaller than 2d.

64. A peripheral intravascular assembly for catheterization (201) comprising:
   a. a tubular introducer needle (202) comprising a connection hub (206) and a needle member (202) having a lumen (212), a distal end (204) and a proximal end (205),
   b. a cannula tubing (203) surrounding at least a portion of the needle member (202),
   c. an electronic module (301) comprising a light source (312; 312*a*),
   d. a light guide (210) having a distal end and a proximal end and extending along the lumen of the needle member (202), wherein the proximal end of the light guide (210) is optically coupled to the light source such that light emitted by the light source (312) is capable of entering the light guide (210),
   e. a pushing mechanism (701) that is configured to push the light guide (210), upon actuation of the pushing mechanism by a user, further through the lumen (212) of the needle member (202) such that the distal end of the light guide projects over the distal end of the needle member (202) at least by a distance b.

65. The assembly of sentence 64, wherein b is greater than 2 mm.

66. The assembly of sentences 64 or 65, wherein b is smaller than 20 mm.

67. The assembly (201) of any of sentences 62 to 66, comprising the features of one of sentences 35 to 61.

68. The assembly (201) of any of the preceding sentences, wherein the distal end of the light guide (210) supports, or is formed by, a positive lens.

69. A peripheral intravascular assembly for catheterization (201) comprising:
 a. a tubular introducer needle (211) comprising a connection hub (206) and a needle member (202), wherein the needle member (202) has a lumen (212), a distal end (204) and a proximal end (205),
 b. a cannula tubing (203) surrounding at least a portion of the needle member (202),
 c. a light source (312; 312a),
 d. an electronic module (301) that is configured to power the light source,
 e. a light guide (210) having a distal end and a proximal end and extending along the lumen of the needle member (202),
 wherein at least 40% of light that contributes to the total light intensity emerging from the distal end of the light guide (210) has a wavelength between 500 nm and 580 nm.

70. A method for an intracutaneous localization of blood vessels, for detection the moment of an intravascular penetration and for safeguarding the blood vessel from being damaged from inside is provided, said method comprises:
 a. locating a blood vessel, suitable to perform vascular access procedure;
 b. obtaining the intravascular assembly for catheterization (201) provided with the electronic module (301);
 c. activating the light source(s) (312) of the electronic module (301) for light to be observed on the distal end (204) of the needle member (202) of the introducer needle (211);
 d. puncturing the skin with the introducer needle (211) of the intravascular assembly for catheterization (201);
 e. localizing a blood vessel position intracutaneously by monitoring illumination events at the distal end (204) of the needle member (202) of the introducer needle (211);
 f. detecting the moment when the distal end (204) of the needle member (202) of the introducer needle (211) penetrates the wall of a blood vessel and enters the lumen of a blood vessel by observing at least one of the following illumination events at the introducer needle distal end (204): instant disappearance of illumination, rapid illumination fading, rapid change in light color and/or rapid illumination fading along with rapid change in light color, wherein said events are dependent on the light wavelength utilized;
 g. ensuring a correct position of the introducer needle (211) inside a blood vessel lumen by monitoring illumination events at the introducer needle distal end (204);
 h. advancing a cannula tubing (203) into a lumen of blood vessel;
 i. following the advancement of the cannula tubing (203) into a lumen of blood vessel by monitoring illumination events at the distal end of said cannula tubing.

71. A method for placing an intravascular catheter into a blood vessel, said method comprises:
 a. locating a blood vessel, suitable to perform vascular access procedure;
 b. visual or performed by palpation condition determination of a blood vessel to be punctured;
 c. obtaining the intravascular assembly for catheterization (201) provided with the electronic module (301);
 d. activating the light source(s) (312) of the electronic module (301) for light to be observed on the distal end (204) of the needle member (202) of the introducer needle (211);
 e. puncturing the skin with the introducer needle (211) of the intravascular assembly for catheterization (201);
 f. localizing a blood vessel position intracutaneously by monitoring illumination events at the distal end (204) of the needle member (202) of the introducer needle (211);
 g. detecting the moment when the distal end (204) of the needle member (202) of the introducer needle (211) penetrates the wall of a blood vessel and enters the lumen of a blood vessel by observing at least one of the following illumination events at the introducer needle distal end (204): instant disappearance of illumination, rapid illumination fading, rapid change in light color and/or rapid illumination fading along with rapid change in light color, wherein said events are dependent on the light wavelength utilized;
 h. ensuring a correct position of the introducer needle (211) inside a blood vessel lumen by monitoring illumination events at the introducer needle distal end (204);
 i. extending a cannula tubing (203) inside a blood vessel lumen;
 j. following the advancement of the cannula tubing (203) into a blood vessel lumen by monitoring illumination events at the distal end of said cannula tubing;
 k. withdrawing the introducer needle (211) from a blood vessel, while the cannula tubing (203) is set inside a blood vessel;
 l. securing the cannula tubing (203) over the skin of a patient and connecting an appropriate system thereto.

72. The catheter assembly of any of the preceding sentences, wherein at least 70% of light contributing to the total light intensity emitted from the distal end of the introducer needle has a wavelength between 510 nm and 610 nm, preferably at least 60% of light, contributing to the total intensity emitted from the distal end of the introducer needle has a wavelength selected from one of the following ranges: between 510 nm and 572 nm, or 524 nm and 586 nm, or 546 nm and 608 nm.

73. The catheter assembly of any of the preceding sentences, wherein at least 70% of light contributing to the total light intensity emitted from the distal end of the introducer needle has a wavelength between 510 nm and 600 nm, preferably at least 50% of light, contributing to the total intensity emitted from the distal end of the introducer needle has a wavelength selected from one of the following ranges: between 510 nm and 550 nm, or 530 nm and 570 nm, or 560 nm and 600 nm.

74. The catheter assembly of any of the preceding sentences, wherein at least 60% of light, contributing to the total intensity emitted from the distal end of the introducer needle has a wavelength selected from one of the following ranges: between 510 nm and 572 nm, or 524 nm and 586 nm, or 546 nm and 608 nm.

75. The catheter assembly of any of the preceding sentences, wherein at least 40% of light contributing to the total light intensity emitted from the distal end of the introducer needle has a wavelength between 510 nm and 600 nm, preferably at least 30% of light, contributing to the total intensity emitted from the distal end of the introducer needle has a wavelength selected from one of the following ranges: between 510 nm and 550 nm, or 530 nm and 570 nm, or 560 nm and 600 nm.

76. The catheter assembly of any of the preceding sentences, wherein at least 50% of light, contributing to the total intensity emitted from the distal end of the introducer needle has a wavelength selected from one of the following ranges: between 510 nm and 550 nm, or 530 nm and 570 nm, or 560 nm and 600 nm.

77. A intravascular assembly for catheterization (201) comprising:
 a. an introducer needle (211) comprising a connection hub (206) and a needle member (202), wherein the needle member (202) has a lumen (212), a distal end (204) provided with an blood entry aperture (204a) and a proximal end (205),
 b. a light guide (210) having a distal end and a proximal end and extending along the lumen of the needle member (202),
 c. an adapter (209) to which the light guide (210) is fixed or mounted,
 wherein the adapter (209) is provided with an interface for a light source,
 wherein the adapter (209) is connected to the connection hub (206) of the introducer needle (211),
 wherein the adapter (209) is adapted to form a leak-proof barrier between blood and an interface for a light source.

78. The assembly of sentence 77, wherein the distal end of the light guide (210) is arranged inside the lumen (212) of the needle member (202) and terminates anywhere within the distal end (204) of the needle member, including outside of the blood entry aperture (204a) in the area limited by the tip (204b).

79. The assembly of any of the preceding sentences 77 to 78, wherein the distal end of the light guide (210) is arranged inside the lumen (212) of the needle member (202), but spaced proximally apart from the blood entry aperture (204a) at the distal end (204) of the needle member (202) by a distance that is greater than 0.1 mm and smaller than 20 mm.

80. The assembly of any of the preceding sentences 77 to 79, comprising a pushing mechanism (701) that is configured to move the light guide (210), upon actuation of the pushing mechanism by a user, along the lumen (212) of the needle member (202) between a retracted position, in which the distal end of the light guide (210) is positioned inside the distal end (204) of the needle member (202), and a projecting position, in which the distal end of the light guide (210) projects through the blood entry aperture (204a) of the needle member (202) at least by a distance 2d, wherein d is the minimal diameter of the lumen (212) of the needle member (202).

81. The assembly of any of the preceding sentences 77 to 80 further comprising a cannula tubing (203) surrounding at least a portion of the needle member (202).

82. The assembly of any of the preceding sentences 77 to 81 further comprising at least one light source (312; 312a).

83. The assembly of any of the preceding sentences 77 to 82, comprising at least two separate light sources (312a; 312b) that are configured to be operated simultaneously and/or subsequently.

84. The assembly of any of the preceding sentences 77 to 83, wherein at least one light source (312; 312a; 312b) is fixed or mounted at the adapter (209).

85. The assembly of any of the preceding sentences 77 to 84, wherein at least one light source (312; 312a; 312b) is fixed or mounted at the proximal end of the light guide (210) so, that light emitted by said light source can enter the light guide (210) or be transmitted into the light guide preferably at its proximal end.

86. The assembly of any of the preceding sentences 77 to 85, wherein the adapter (209) is connectable or connected to at least one light source (312; 312a; 312b) so, that light emitted by said light source can enter the light guide (210) or be transmitted into the light guide preferably at its proximal end, and wherein the adapter (209) forms a leak-proof barrier between blood and said light source.

87. The assembly of any of the preceding sentences 77 to 86 further comprising at least one electronic module (301) that is configured to power at least one light source (312; 312a; 312b).

88. The assembly of any of the preceding sentences 77 to 87, wherein at least one light source (312; 312a; 312b) is arranged within the electronic module (301).

89. The assembly of any of the preceding sentences 77 to 88, wherein the adapter (209) is provided with an interface for an electronic module, 90. The assembly of any of the preceding sentences 77 to 89, wherein the electronic module (301) is fixed or mounted at the adapter (209).

91. The assembly of any of the sentences 77 to 83 and 85 to 90, wherein the electronic module (301) is fixed or mounted at the proximal end of the light guide (210).

92. The assembly of any of the preceding sentences, wherein the adapter (209) is connectable or connected to the electronic module (301) so, that light emitted by at least one light source (312, 312a; 312b) can enter the light guide (210) or be transmitted into the light guide preferably at its proximal end, and wherein the adapter (209) forms a leak-proof barrier between blood and said light source.

93. The assembly of any of the preceding sentences, wherein the adapter (209) comprises at least two adapter parts being connected or connectable to each other, and wherein the first adapter part is connected or connectable with the connection hub (206) and the second adapter part is connected or connectable with the electronic module (301).

94. The assembly of any of the preceding sentences, wherein at least one adapter part is integrally formed as one functional unit with the electronic module (301).

95. The assembly of any of the sentences 77 to 93, wherein at least one adapter part is integrally formed as one functional unit with the introducer needle (211).

96. The assembly of any of the sentences 77 to 93, wherein at least one adapter part forms an integral functional unit with the electronic module (301) and the introducer needle (211).

97. The assembly of any of the sentences 77 to 93, wherein at least one adapter part is integrally formed as one functional unit with the needle member (202).

98. The assembly of any of the sentences 77 to 96, wherein the adapter (209) is arranged at a distance from the proximal end of the needle member (202).

99. The assembly of any of the preceding sentences 77 to 98, comprising safety means for preventing a user of being wounded by the distal end (204) of the needle member (202), wherein said safety means are configured as an automatic retraction-extension mechanism for the light guide (210) comprising the adapter being configured as a two-unit member, which comprises an outer unit (219), which has a central aperture (219a), and a central unit (229), which is positioned within the central aperture (219a) of the outer unit, wherein the central unit (229) is configured to be movable within the aperture (219a) of the outer unit and is provided with a bore (229a) to receive the light guide (210), said bore (229a) being sealed liquid-tightly against the light guide (210), wherein an operation of the automatic retraction-extension mechanism is based on automatic rotational and/or translational movement of the central unit (229) within the aperture (219a) of the outer unit (219) upon mounting or dismounting the introducer needle (211) onto the electronic module (301) or from the electronic module (301), respectively.

100. The assembly of any of the preceding sentences 77 to 99, wherein the maximal diameter of the circumscribed circle along at least 1 mm length of the adapter (209) is larger than the maximal diameter of the circumscribed circle of at least the most proximal 7 mm length of the connection hub (206) of the introducer needle (211), wherein circumscribed circles are regarded to be only in planes orthogonal to the introducer needle (211) axis.

101. The assembly of any of the preceding sentences 77 to 100, wherein the connection hub (206) is provided with an inner chamber, in particular, a flashback chamber and wherein the proximal end (205) of the needle member (202) is arranged at or within the inner chamber of the connection hub so, that blood flowing from the blood entry aperture (204a) of the distal end (204) through the lumen (212) of the needle member (202) will exit the proximal end (205) of the needle member and enter or be received by the inner chamber of the connection hub (206) and wherein the adapter (209) provides a sealing for the light source from blood in the inner chamber.

102. The assembly of sentence 101, wherein the connection hub is provided with a flashback chamber (207) as the inner chamber for receiving blood exiting from the proximal end of the needle member.

103. The assembly of any of the sentences 101 or 102, wherein an inner chamber, such as a flashback chamber (207), has a body portion shaped as a funnel, wherein the proximal end (205) of the needle member (202) of the introducer needle (211) is integrated within the vertex of the funnel and terminates therein so as to allow a fast and accurate insertion of the light guide (210) into the needle member (202) via connection hub (206).

104. The assembly of any of the preceding sentences 77 to 103, comprising a separate member (320) positioned inside the connection hub (206), said separate member (320) being configured as a double sided funnel having two funnel bases pointing to opposite directions, wherein the funnel comprises a central through-bore ending at apertures on both funnel bases, wherein an inner diameter of the bore is adapted to allow free sliding of the light guide (210) therethrough, and wherein the apertures on both bases of the funnel are substantially coaxial to the proximal end (205) of the needle member (202) so as to allow a smooth insertion of the light guide (210) into the needle member (202) via the connection hub (206).

105. The assembly of any of the preceding sentences 77 to 104, wherein a connection between the adapter (209) and the connection hub (206) of the introducer needle (211) and/or the electronic module (301) is liquid-tight, in particular blood-tight.

106. The assembly of any of the preceding sentences 77 to 105, wherein the light guide (210) is an optical fiber.

107. The assembly of any of the preceding sentences 77 to 106, wherein the light guide (210) is received in the lumen (212) of the needle member (202) such that the light guide is capable of sliding along the lumen if a tensile force is applied to one end of the light guide.

108. The assembly of any of the preceding sentences 77 to 107, wherein the light guide (210) is arranged to extend through the adapter (209).

109. The assembly of any of the sentences 101 or 102, wherein the inner chamber of the connection hub (206) and/or the proximal end (205) of the needle member (202) is/are arranged at a distal side of the adapter (209D) and the proximal end of the light guide (210) is arranged at the proximal side of the adapter (209P) opposite to the distal side (209D).

110. The assembly of any of the sentences 101, 102 or 109, wherein the adapter (209) is arranged in between the inner chamber of the connection hub and the light source (312; 312a; 312b) thus separating thereof.

111. The assembly of any of the preceding sentences 77 to 110, further comprising a sealing around the light guide (210) within the lumen (212) of the needle member (202) substantially at the proximal end (205) of the needle member (202) or outside the lumen (212) of the needle member (202) at the proximal end (202) thereof.

112. The assembly of any of the preceding sentences 77 to 111, wherein the introducer needle (211) is tubular.

113. The assembly of any of the preceding sentences 77 to 112 further comprising an additional aperture in the wall of the connection hub of the introducer needle, which aperture is sealed with a liquid tight, in particular blood tight material, to form an air escape window allowing blood to collect inside the flashback chamber (207) and air to escape from an inner volume of the connection hub.

114. The assembly of any of the preceding sentences 77 to 113 further comprising an additional aperture in the adapter at least partially sealed with material creating liquid tight, in particular liquid tight air escape window allowing collection of blood inside of the flashback chamber (107) and escape of air from the inner volume of the connection hub.

115. The assembly of any of the preceding sentences 77 to 114 further comprising an ON/OFF switching mechanism, capable of automatic activation of at least one light source (312, 312a; 312b) upon mounting electronic module with catheter assembly or adapter.

116. The assembly of the sentence 115 comprising an ON/OFF switching mechanism, capable of automatic deactivation of the light source upon dismounting electronic module from introducer needle or adapter.

117. The assembly of any of the preceding sentences 77 to 116 further comprising a connection interface between connection hub of the introducer needle and the electronic module.

118. The assembly of any of the preceding sentences 77 to 117 where the adapter (209) is releasably connected to the connection hub of the introducer needle thus providing a possibility to separate the introducer needle from the adapter.

119. The catheter assembly of any of the preceding sentences 77 to 118, wherein at least 40% of light contributing to the total light intensity emitted from the distal end of the introducer needle has a wavelength between 510 nm and 610 nm, preferably at least 30% of light, contributing to the total intensity emitted from the distal end of the introducer needle has a wavelength selected from one of the following ranges: between 510 nm and 572 nm, or 524 nm and 586 nm, or 546 nm and 608 nm.

120. The catheter assembly of any of the preceding sentences 77 to 119, wherein at least 70% of light contributing to the total light intensity emitted from the distal end of the introducer needle has a wavelength between 510 nm and 610 nm, preferably at least 50% of light, contributing to the total intensity emitted from the distal end of the introducer needle has a wavelength selected from one of the following ranges: between 510 nm and 572 nm, or 524 nm and 586 nm, or 546 nm and 608 nm.

121. The catheter assembly of any of the preceding sentences 77 to 120, wherein at least 60% of light, contributing to the total intensity emitted from the distal end of the introducer needle has a wavelength selected from one of the following ranges: between 510 nm and 572 nm, or 524 nm and 586 nm, or 546 nm and 608 nm.

122. The catheter assembly of any of the preceding sentences 77 to 121, wherein the intravascular assembly for catheterization is a peripheral intravascular assembly for catheterization.

123. The catheter assembly of any of the preceding sentences 77 to 122 for use in an intracutaneous localization of blood vessels and/or for detection the moment of an intravascular penetration and/or for safeguarding the blood vessel from being damaged from inside.

124. A method for assembling a peripheral intravascular assembly for catheterization, said method comprises:
 a. providing the adapter (209) and the light guide (210);
 b. pre-mounting or fixing the light guide (210) to the adapter (209) so, that a distal end and a following proximally extending towards the adapter section of the light guide are accessible;
 c. providing the introducer needle (211);
 d. inserting the distal end and the following proximally extending towards the adapter section of the light guide (210) from the proximal end (205) of the needle member (202) into its lumen (212) so, that the light guide (210) extends through the lumen (212);
 e. leak-proof connecting the adapter (209) to the connection hub (206) of the introducer needle (211).

125. A method for an intracutaneous localization of blood vessels, for detection the moment of an intravascular penetration and for safeguarding the blood vessel from being damaged from inside, said method comprises:
 a. locating a blood vessel, suitable to perform vascular access procedure;
 b. obtaining the peripheral intravascular assembly for catheterization (201) provided with the electronic module (301) with at least one light source (312, 312a);
 c. activating at least one light source (312, 312a) of the electronic module (301) for light to be observed on the distal end (204) of the needle member (202) of the introducer needle (211);
 d. puncturing the skin with the introducer needle (211) of the intravascular catheter assembly (201);
 e. localizing a blood vessel position intracutaneously by monitoring illumination events at the distal end (204) of the needle member (202) of the introducer needle (211);
 f. detecting the moment when the distal end (204) of the needle member (202) of the introducer needle (211) penetrates the wall of a blood vessel and enters the lumen of a blood vessel by observing at least one of the following illumination events at the introducer needle distal end (204): instant disappearance of illumination, rapid illumination fading, rapid change in light color and/or rapid illumination fading along with rapid change in light color, wherein said events are dependent on the light wavelength utilized;
 g. ensuring a correct position of the introducer needle (211) inside a blood vessel lumen by monitoring illumination events at the introducer needle distal end (204);
 h. advancing a cannula tubing (203) into a lumen of blood vessel.

The invention claimed is:

1. An intravascular assembly for catheterization comprising:
 a. an introducer needle comprising a connection hub and a needle member, wherein the needle member has a lumen, a distal end provided with a blood entry aperture, and a proximal end, and wherein the connection hub defines an inner chamber adapted to receive blood exiting from the proximal end of the needle member;
 b. a light guide having a distal end and a proximal end and extending along the lumen of the needle member, wherein the distal end of the light guide is arranged inside the lumen of the needle member;
 c. an adapter secured to the light guide, wherein the light guide is arranged to extend through the adapter; and
 d. at least one light source,
wherein the adapter is provided with an interface for the at least one light source, wherein the adapter is connected to the connection hub of the introducer needle,
wherein the adapter is adapted to form a leak-proof barrier between blood within the inner chamber of the connection hub and the at least one light source,
wherein the proximal end of the light guide is optically coupled to the at least one light source such that light emitted by the at least one light source enters the light guide and is emitted by the distal end of the needle member, and
wherein the light emitted from the distal end of the needle member has a total light intensity, and wherein at least 70% of the light emitted from the distal end of the needle member has a wavelength between 510 nm and 610 nm.

2. The assembly of claim 1, wherein the distal end of the light guide is arranged inside the lumen of the needle member, but spaced proximally apart from the blood entry aperture at the distal end of the needle member by a distance that is greater than 0.1 mm and smaller than 20 mm.

3. The assembly of claim 1, further comprising a cannula tubing surrounding at least a portion of the needle member.

4. The assembly of claim 1, further comprising at least one electronic module that is configured to power the at least one light source.

5. The assembly of claim 4, wherein the lumen of the needle member has a minimal diameter, the assembly further comprising a pushing mechanism that is configured to move the light guide, upon actuation of the pushing mechanism by a user, along the lumen of the needle member between a retracted position, in which the distal end of the light guide is positioned inside the distal end of the needle member, and a projecting position, in which the distal end of the light guide projects through the blood entry aperture of the needle member by a distance that is at least twice the minimal diameter of the lumen of the needle member.

6. The assembly of claim 4, wherein the at least one light source comprises at least two separate light sources that are configured to be operated independently.

7. The assembly of claim 4, wherein the at least one light source is arranged within the electronic module.

8. The assembly of claim 4, wherein the adapter (209) is provided with an interface for the electronic module.

9. The assembly of claim 4, wherein the electronic module is secured at the adapter.

10. The assembly of claim 9, further comprising an ON/OFF switching mechanism, wherein the ON/OFF switching mechanism is configured to automatically activate the at least one light source upon mounting the electronic module with the adapter.

11. The assembly of the claim 10, wherein the ON/OFF switching mechanism is configured to automatically deactivate the at least one light source upon dismounting the electronic module from the adapter.

12. The assembly of claim 4, wherein the adapter is connectable to the electronic module so that the light emitted by the at least one light source is transmitted into the light guide.

13. The assembly of claim 4, wherein the adapter comprises at least two adapter parts that are connectable to each other, and wherein the first adapter part is connectable with the connection hub and the second adapter part is connectable with the electronic module.

14. The assembly of claim 4, wherein the adapter is configured as a two-unit member comprising an outer unit having a central aperture and a central unit positioned within the central aperture of the outer unit, wherein the central unit is configured to be movable within the aperture of the outer unit and is provided with a bore to receive the light guide, wherein the bore is sealed liquid-tightly against the light guide, wherein operation of the adapter is based on automatic movement of the central unit within the aperture of the outer unit upon mounting the introducer needle onto the electronic module or dismounting the introducer needle from the electronic module.

15. The assembly of claim 1, wherein the light guide is an optical fiber.

16. The assembly of claim 1, wherein the adapter is releasably connected to the connection hub of the introducer needle to permit separation of the introducer needle from the adapter.

17. The assembly of claim 1, wherein at least 60% of light contributing to the total intensity emitted from the distal end of the introducer needle has a wavelength selected from one of the following ranges: between 510 nm and 572 nm, or 524 nm and 586 nm, or 546 nm and 608 nm.

18. The assembly of claim 1, wherein the light guide is fixed in a position in which the distal end of the light guide is spaced proximally from the blood entry aperture at the distal end of the needle member.

19. A method for accessing a blood vessel of a subject, the method comprising:
a. locating a blood vessel suitable to perform vascular access procedure;
b. activating at least one light source of an intravascular assembly, the intravascular assembly comprising:
an introducer needle comprising a connection hub and a needle member, wherein
the needle member has a lumen, a distal end provided with a blood entry aperture, and a proximal end, and wherein the connection hub defines an inner chamber adapted to receive blood exiting from the proximal end of the needle member;
a light guide having a distal end and a proximal end and extending along the lumen of the needle member, wherein the distal end of the light guide is arranged inside the lumen of the needle member;
an adapter secured to the light guide, wherein the light guide is arranged to extend through the adapter; and
at least one light source,
wherein the adapter is provided with an interface for the at least one light source, wherein the adapter is connected to the connection hub of the introducer needle,
wherein the adapter is adapted to form a leak-proof barrier between blood within the inner chamber of the connection hub and the interface for the at least one light source,
wherein the proximal end of the light guide is optically coupled to the at least one light source such that light emitted by the at least one light source enters the light guide and is emitted by the distal end of the needle member, and
wherein the light emitted from the distal end of the needle member has a total light intensity, and wherein at least 70% of the light emitted from the distal end of the needle member has a wavelength between 510 nm and 610 nm
c. puncturing skin with the introducer needle;
d. localizing a blood vessel position intracutaneously by monitoring illumination at the distal end of the needle member of the introducer needle;
e. detecting when the distal end of the needle member of the introducer needle penetrates a wall of the blood vessel and enters a lumen of the blood vessel by observing a change in illumination at the distal end of the needle member; and
f. ensuring a correct position of the introducer needle inside the lumen of the blood vessel by monitoring illumination at the distal end of the introducer needle.

20. The method of claim 19, wherein the observed change in illumination at the distal end of the needle member comprises at least one of: a disappearance of illumination; a fading of illumination; or a change in light color.

* * * * *